(12) United States Patent
Wang et al.

(10) Patent No.: US 9,076,104 B2
(45) Date of Patent: Jul. 7, 2015

(54) SYSTEMS AND METHODS FOR IDENTIFYING DRUG TARGETS USING BIOLOGICAL NETWORKS

(71) Applicant: The Regents of the University of California, Oakland, CA (US)

(72) Inventors: Wei Wang, La Jolla, CA (US); Rui Chang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 22 days.

(21) Appl. No.: 13/680,297

(22) Filed: Nov. 19, 2012

(65) Prior Publication Data

US 2013/0151452 A1 Jun. 13, 2013

Related U.S. Application Data

(63) Continuation of application No. PCT/US2011/037001, filed on May 18, 2011.

(60) Provisional application No. 61/346,182, filed on May 19, 2010.

(51) Int. Cl.
*G06N 5/02* (2006.01)
*G06F 19/18* (2011.01)
*G06F 19/12* (2011.01)

(52) U.S. Cl.
CPC ...... *G06N 5/02* (2013.01); *G06F 19/18* (2013.01); *G06F 19/12* (2013.01)

(58) Field of Classification Search
None
See application file for complete search history.

(56) References Cited

U.S. PATENT DOCUMENTS

| | | | |
|---|---|---|---|
| 2003/0219764 A1 | 11/2003 | Imoto et al. | |
| 2004/0254903 A1* | 12/2004 | Heckerman et al. | 706/46 |
| 2005/0021237 A1 | 1/2005 | Schachter et al. | |
| 2005/0119534 A1 | 6/2005 | Trost et al. | |
| 2006/0212279 A1 | 9/2006 | Goldberg et al. | |
| 2008/0220977 A1* | 9/2008 | Imoto et al. | 506/2 |
| 2009/0036757 A1 | 2/2009 | Brockway et al. | |
| 2010/0318490 A1* | 12/2010 | Bouchard et al. | 706/52 |
| 2011/0040713 A1* | 2/2011 | Colman et al. | 706/16 |
| 2011/0161278 A1* | 6/2011 | Kawagishi | 706/52 |
| 2011/0289042 A1* | 11/2011 | Chan et al. | 706/52 |

OTHER PUBLICATIONS

PCT International Search Report for PCT Application No. PCT/US2011/037001 mailed Feb. 9, 2012 (2 pages).

* cited by examiner

*Primary Examiner* — Jeffrey A Gaffin
*Assistant Examiner* — Mikayla Chubb
(74) *Attorney, Agent, or Firm* — Sutherland Asbill & Brennan LLP

(57) ABSTRACT

Certain embodiments of the invention may include systems and methods for identifying drug targets using biological networks. According to an example embodiment of the invention, a method is provided for predicting the effects of drug targets on treating a disease. The method can include constructing a structure of a Bayesian network based at least in part on knowledge of drug inhibiting effects on a disease; associating a set of parameters with the constructed Bayesian network; determining values of a joint probability distribution of the Bayesian network via an automatic procedure; deriving a mean Bayesian network with one or more averaged parameters based at least in part on the joint probability values; and calculating a quantitative prediction based at least in part on the mean Bayesian network.

7 Claims, 22 Drawing Sheets

SYSTEMS AND METHODS FOR IDENTIFYING DRUG TARGETS USING BIOLOGICAL NETWORKS

CROSS REFERENCES TO RELATED APPLICATIONS

This application is a continuation of PCT Application No. PCT/US2011/037001 filed on May 18, 2011, which claims priority from U.S. Provisional Application Ser. No. 61/346,182 filed on May 19, 2010, each of which is incorporated herein by reference in its entirety.

STATEMENT FOR GOVERNMENT SUPPORT

The invention was made with government support under Grant No. GM 072856 awarded by the National Institutes of Health. The U.S. government has certain rights to the invention.

FIELD OF INVENTION

This invention relates to systems biology. More particularly, the invention provides a systematic way, based on biological networks, to evaluate the effects of inhibiting multiple drug targets on treating a disease.

BACKGROUND OF THE INVENTION

Bayesian networks (BN) are a popular class of graphical probabilistic models which are motivated by Bayes theorem. Such networks have been increasingly applied to various computation applications, such as computational biology and computer vision. Current Bayesian network parameter learning approaches can be classified into two categories: frequentist approach with maximum likelihood (ML) estimation, and a Bayesian approach with maximum a posterior (MAP) estimation. ML only uses statistical counts from the data to estimate the parameters in a Bayes net while MAP employs certain type of priori statistical belief to further regulate the statistical counts from the data. Therefore, MAP parameter estimation is a combinatorial result computed from both data and prior knowledge.

Prior knowledge can be loosely defined as any statements involving network structure and parameter properties. For example, a domain expert can provide information on a local structure by specifying conditional independence among a subset of variables or even fully specifying the causality between variables, thus direction of this edge. A domain expert might also provide knowledge on network parameters ranging from directly assigning values to entries in a conditional probability table (CPT) to introducing inequality and equality constraints in one distribution or across multiple conditional distributions. In addition, domain knowledge might also define a prior distribution over the parameters. Moreover, some knowledge imposes equality and inequality constraints over the hyperparameters in the prior distribution function.

Among various domain knowledge, qualitative statements are perhaps the most generic and intuitive information in a domain. These statements describes (in)dependence and causality among domain variables. By definition, "(in)dependence" links multiple entities in a joint representation and "causality" specifies the conditions and direction within this joint set. In Bayesian framework, the (in)dependence and causality in the qualitative domain knowledge defines a set of inequality relation(s) between a child node's probabilities given all possible conFig.s of its parents. Since nearly every BN admits (in)dependence and causality given structure, this type of constraints provide the most generic and useful priori constraints to the parameter learning task. Moreover, it is less demanding for a domain expert to specify an inequality constraint over entries in a CPT than giving specific values on individual entry or defining the hyper-parameters of a Dirichlet prior.

Researchers have proposed a number of algorithms to learn Bayesian network parameters by utilizing various forms of prior knowledge, such as dirichlet function[2], [3]. In certain references [4], [5], [6], parameter learning schemes for various graphical models incorporating parameter sharing constraints is proposed. For example, parameter equality in one multinomial conditional distribution. The forms of the constraints are limited to either parameter sharing or inequality constraints within one conditional distribution, such as $P(A|B) > P(A|\sim B)$. More generic and important inequality constraints, such as $P(A|B) > P(A|\sim B)$ is not addressed by their methods. In other references [10] and [11], methods are proposed to deal with the inequality constraints in parameter learning.

Thus, the inequality constraints have been proposed and used in qualitative probabilistic inference [18], [19]. However, due to the lacks of quantitative measurements in the constraints, they have long been ignored in incorporating with the quantitative training data in any BN learning process.

The current drug development strategy is primarily focused on developing tight inhibitors for a single target, which may not be the most effective way to treat a disease. The recent advancement of systems biology clearly demonstrated that the genes/proteins are tightly connected to each other. The role of a drug target in the genetic network is no doubt a determinant factor for the efficacy of the inhibitor(s). In addition, considering the redundancy and robustness of the genetic network, effective treatment of a disease may require simultaneous inhibition of multiple proteins. Developing pharmaceutical targeting a set of proteins in a pathway will open a new territory in drug discovery and will be a trend in the near future.

Given the complexity of genetic networks, it is difficult, if not impossible, to manually select a combination of proteins as the drug targets and predict the effects of inhibiting these proteins. Therefore, a computational approach that can tackle this problem in a systematic and unbiased manner is needed for pharmaceutical companies that are constantly searching for new drug targets.

SUMMARY OF THE INVENTION

Some or all of the above needs may be addressed by certain embodiments of the invention. Certain embodiments of the invention may include systems and methods for identifying drug targets using biological networks According to an example embodiment of the invention, a method is provided for predicting the effects of drug targets on treating a disease is provided. The method can include constructing a structure of a Bayesian network based at least in part on knowledge of drug inhibiting effects on a disease; associating a set of parameters with the constructed Bayesian network; determining values of a joint probability distribution of the Bayesian network via an automatic procedure; deriving a mean Bayesian network with one or more averaged parameters based at least in part on the joint probability values; and calculating a quantitative prediction based at least in part on the mean Bayesian network.

According to another example embodiment of the invention, a method is provided for automatically determining a multinomial distribution in a Bayesian network. The method includes constructing a graphical structure of a Bayesian network using a set of joint probability parameters associated to the constructed Bayesian network structure; designing an automatic procedure to determine values associated with said joint probability parameters; simultaneously deriving an equivalent mean Bayesian network or a class of Bayesian networks; and performing quantitative predictions and reasoning simulations using the equivalent mean Bayesian network or the class of Bayesian networks.

According to an example embodiment of the invention, a system is provided for determining parameters of a Bayesian network. The system may include at least one memory for storing executable instructions; at least one processor in communication with the at least one memory, wherein the at least one processor is operable to execute the stored instructions to receive a plurality of inequality parameter constraints, the inequality constraints based at least in part on qualitative domain knowledge; construct a parameter distribution based upon the plurality of inequality parameter constraints; and integrate, using quantitative data statistics, the parameter distribution to determine a Bayesian parameter score function using quantitative domain knowledge, wherein the Bayesian parameter score function reflects both the quantitative domain knowledge and the qualitative domain knowledge.

Example embodiments of the invention provide an algorithm or procedure for performing parameter learning in Bayesian network given structure by integrating qualitative statements-derived inequality constraint with data. An example algorithm provided by an embodiment of the invention can handle many other types of prior knowledge and constraints, such as undirected relation, logic and higher-order non-linear constraints. Even with the most generic constraints, example embodiments of the invention can dramatically improve learning accuracy even with very scarce data (a few samples).

Comparatively, the invention method works directly on the parameter space through sampling and obtain the dirichlet hyperparameters directly. Thus, the invention method can be more efficient and feasible than some traditional methods [13]. Besides the data-based learning approaches with prior knowledge, a novel algorithm is provided to perform quantitative probabilistic inference in (Dynamic) Bayesian networks by using only prior knowledge (without any quantitative training data) [7]. Using example embodiments of the invention, it is possible to represent various inequality relations between conditional probabilities with linear regression [7]. Parameter constraints may be used to define a distribution in the model space where each model is consistent with the body of the prior knowledge. Inconsistent knowledge can be transformed into a distribution over the knowledge space [8].

Example embodiments of the invention provide a computational method to identify drug targets using a systems biology approach. Given a network that regulates a disease, the invention method can predict the effects of inhibiting a set of genes on the marker genes of the disease. For example, if two marker genes are highly up-regulated in a disease, the invention method can find inhibition of which genes can reduce the expression of the two marker genes back to the normal levels. Therefore, the invention method provides a systematic approach to identifying drug targets. More particularly, example embodiments of the invention provide a systematic way, based on biological networks, to evaluate the effects of inhibiting multiple drug targets on treating a disease. Such effects often cannot easily identified by using traditional molecular biology approach.

Different from the commonly used approach of modeling network behavior using ordinary or partial differential equation (ODE or PDE), example embodiments do not require any free parameter like the rate constants used in ODE or PDE. This feature makes it possible to model large networks (hundreds of nodes) and analyze the consequences of simultaneous perturbation of multiple genes. In contrast, ODE or PDE are often limited to analyzing a relatively much smaller network (10-20 nodes).

The capability of analyzing large network is important in drug target discovery because the genetic network regulating a disease often involves a large number of genes. Therefore, ODE or PDE approaches only can consider local effects in the network. However, embodiments of the invention can take into account global effects of inhibiting proteins in the network and therefore, may be useful in drug target discovery.

In certain embodiments, the invention provides a computer-aided procedure for automatic determining numerical parameters in Bayesian networks given the network structure. This is the important step of predicting the effects of inhibiting proteins on marker genes of a disease. In scientific and industrial areas, quantitative simulations are often required to achieve better understanding of a system and to predict system behavior under certain conditions. For example, in genetic-related disease, gene and proteins regulate each other to control the progress of the disease. Inhibiting specific genes/proteins may introduce dramatic changes to the course of the disease. In such case, it is desired to predict such changes in quantitative level with computer-aided simulation algorithms.

According to an example embodiment of the invention, an algorithm is provided that utilizes a Bayesian network, which consist of a structure representing the dependence between the variables in the data and parameters indicating probabilities of occurrence of certain events. In an example embodiment, the Bayesian network can be learned from a set of data where structure and parameters are determined by maximizing certain statistic score. After Bayesian network is established from the data, quantitative prediction on network behavior under specific condition can be investigated. Prerequisites for such quantitative inference may include (i) that the network structure is known, and (ii) that numerical parameters are conFig.d under this structure.

In the practice of drug target discovery, sets of quantitative data are largely unavailable and/or sparse comparing to the dimension of the network. In this case, it is hardly sufficient to learn a Bayesian network from these data, i.e. the learned Bayesian network is statistically insignificant for quantitative predictions. Alternatively, it is still possible to construct a Bayesian network structure by taking advantage of domain experts' knowledge and other knowledge resources in a domain, such as scientific publications. Thus, the remaining problem eventually downgrades to parameter configuration in the constructed network. Without quantitative data, it is almost impossible for domain expert to determine every single probability in the multinomial distribution given the large amount of local structures in a complex Bayesian network. Example embodiments of the invention address such issues by providing a method and/or a computer-aided simulation procedure, to automatically determine the multinomial distribution in a Bayesian network given its structure. According to an example embodiment, the method may include a first step of constructing a graphical structure of a Bayesian network by adding directed edges between variables according to a domain expert and other knowledge resource or by a given or obtained graphical structure before the procedure starts. According to an example embodiment, a set of parameters may be associated with the constructed Bayesian network structure, and the parameters may include joint probability. Each parameter in the set denotes the probability of a value of a variable in a conjunction with values of other variables.

In an example embodiment, the invention may include a second step of designing an automatic procedure to determine the values of the joint probability distribution based on only the (local) structures in a Bayesian network, i.e. the (local) number of activating parents and the (local) number of inhibiting parents. According to an example embodiment, the activating parent, defined as a parent node, when present, may increases the belief of the child node; and the inhibiting parent, defined as a parent node, when present, decrease the belief of the child node. With the determination of the parameter set, example embodiments of the invention may include a third step of deriving an equivalent mean Bayesian network or a class of Bayesian networks simultaneously. This equivalent single Bayesian network may be a Bayesian network with averaged parameters from the Bayesian network class. Either the equivalent mean Bayesian network or the class of Bayesian networks can be used to perform quantitative predictions and reasoning simulations.

Example embodiments of the invention enables automatic parameter configuration in a Bayesian network given its structure. In particular, and according to an example embodiment, the local structure, i.e. the number of local activating parents and inhibiting parents is the only requisite for such parameter configuration. Then, quantitative prediction can be derived from an equivalent mean Bayesian network or from a class of Bayesian networks. The quantitative predictions have been approved to agree with actual experimental biological data.

In certain example embodiments, the automatic joint distribution configuration may be based on three logic observations: (A) excluding the interactions between parents, the more number of activating parent nodes that a child node has become present/active, the larger belief of a child node can become under the same number of active/present inhibiting parents. (B) Excluding the interactions between parents, the more number of inhibiting parent nodes that a child node has become present/active, the smaller belief of a child node can become under the same number of active/present activating parents. (C) Considering the interactions between specific parents, statements (A) and (B) can be adjusted accordingly to meet the logic provided by the interaction.

In other example embodiments of the invention, the belief/probability of the child node under the condition of specific number of activating and/or inhibiting parent nodes being present may be represented and calculated by the joint distribution of the child node and its parent nodes. In yet other example embodiments of the invention, the basic logic in statements (A), (B) and (C), i.e. logic that number of activating and inhibiting parent nodes being present results in larger or smaller belief of the child node. FIG. 1 depicts such logic encoded into a matrix. The row indicates the number of activating parents of a child node and the column denotes the number of inhibiting parents of a child node. Each element in the matrix is the child's probability under a combination of activating and inhibiting parent nodes which is specified by matrix row/col. index. Various combinations of activating and inhibiting parent nodes confer the instantiations of parent nodes and child nodes in the joint distribution. In other words, all instantiations of joint probability are classified into several categories (each category is an element in the parameter ordering matrix in FIG. 1) based on the number of activating parents and number of inhibiting parents in the instantiation.

According to statements (A), (B) and (C) above, each element in the matrix, i.e. the probability value, is arranged in an ascending order from left to right and descending order from top to bottom as shown in FIG. 1. The joint probability of parents nodes and child node can be determined by sampling in the parameter space following these orders. Preferably, the ascending and descending order covers one or more large relations and/or small relations and/or large/equal relations and/or small/equal relations.

In other example embodiments of the invention, each joint probability sample specifies a Bayesian network, and these samples together define a class of Bayesian networks. Average over the joint probability samples may be determined and a mean Bayesian network with averaged parameter derived. According to an example embodiment of the invention, quantitative prediction is calculated by integration over the set of Bayesian networks and limits of this integration are given by the ascending/descending order matrix in the second step (as provided above). The integration is also multiplied by apriori probability of the Bayesian network in the set with which the parameter is associated. This integration can be approximated by Monte Carlo Simulation and/or Markov chains so that every joint probability parameter conferrd to the ordered matrix is accepted with the same apriori probability. If necessary, it is possible to select different apriori probability in different areas of the joint parameter space under the guidance from domain expert and/or other knowledge resources.

In an example embodiment, a graphical structure with cycles may be given. Such graphical structure does not agree with the definition of DAG (directed acyclic graph) and Bayesian network mentioned above. Therefore, a cyclic graph structure is converted into a temporal development of an acyclic graph structure.

Example embodiments of the invention can be used in numerous applications such as molecular biology, genetic engineering, and finance. A preferential area of application is biological and/or biomedical fields. In these fields, graphical structure is given by expert and other knowledge resources about interactions from a protein to a gene and/or influence from biological molecules on occurrence of disease. The parameter configuration may be derived from the local structure according to the second step.

Example embodiments of the invention include a computer program product with a program code stored on a machine-readable carrier for execution by a computer.

FIG. 2 shows examples of acyclic graph structures occur in a Bayesian network. According to the execution of the first step, given structures $G_1$-$G_5$, their associated joint probabilities can be written as:

$$\Theta_1: P(A,B,C,D); \Theta_2: P(A,B,D); \Theta_3: P(A,B,D); \Theta_4: P(A,D); \Theta_5: P(A,D) \quad \text{Eq. (a1)}$$

Bayesian networks defined by these structures and their parameters can be written as $$B_1=(G_1, \Theta_1); B_2=(G_2, \Theta_2); B_3=(G_3, \Theta_3); B_4=(G_4, \Theta_4); B_5=(G_5, \Theta_5); \quad \text{Eq. (a2)}$$

By execution of the second step, a matrix is constructed which places a relative order over the child's probability under a combination of activating and inhibiting parent nodes as shown in FIG. 3A-3E.

According to an example embodiment, value $P_{i,j}$ in the matrix indicates child's probability in the presence of j activating parent nodes and i inhibiting parent nodes. This value may be represented by the joint probability. For example, in FIG. 3D, $P_{0,0}$ and $P_{0,1}$ is calculated as:

$$P_{0,0} = \frac{P(D,\bar{A})}{P(D,\bar{A}) + P(\bar{D},\bar{A})} \qquad \text{Eq. (a3)}$$

$$P_{0,1} = \frac{P(D,A)}{P(D,A) + P(\bar{D},A)} \qquad \text{Eq. (a4)}$$

According to the matrix, the order between the four joint probabilities in Eq. (3), (4) is:

$$\frac{P(D,\bar{A})}{P(D,\bar{A}) + P(\bar{D},\bar{A})} \le \frac{P(D,A)}{P(D,A) + P(\bar{D},A)} \qquad \text{Eq. (a5)}$$

It is also well-known that four joint probability sum to 1 according to probability theory:

$$P(D,\bar{A}) + P(D,A) + P(\bar{D},A) + P(\bar{D},\bar{A}) = 1 \qquad \text{Eq. (a6)}$$

According to the third step of the present invention procedure, each joint probability sample together with the structure $G_4$ uniquely define a Bayesian network $B_4$. These networks forms a class of Bayesian network which generate quantitative predictions and final quantitative result is the numerical average of these predictions. In addition, the average of these joint probability samples results in an equivalent mean Bayesian network. This equivalent Bayesian network is used to generate quantitative prediction.

DETAILED DESCRIPTION OF THE INVENTION

Figure 1:
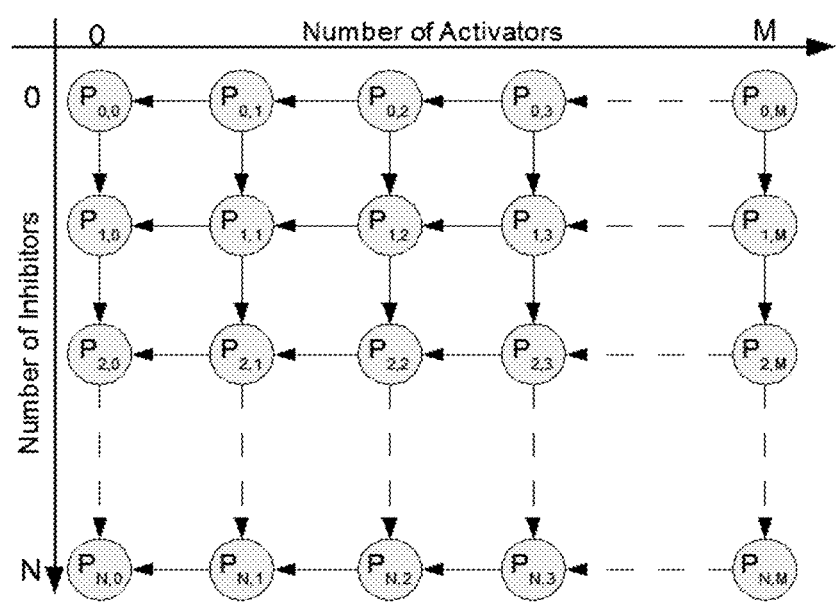
FIG. 1 illustrates parameter ordering matrix based on local structure.
Figure 2:
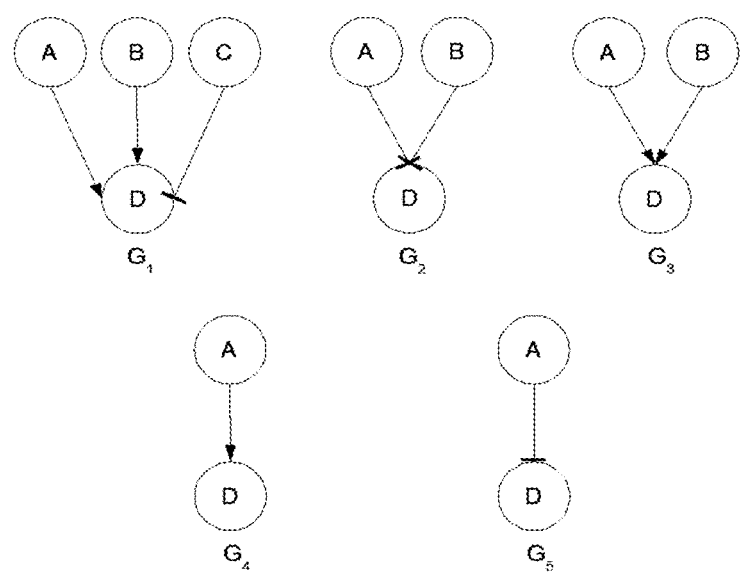
FIG. 2 illustrates graph structure examples.
Figure 3A:
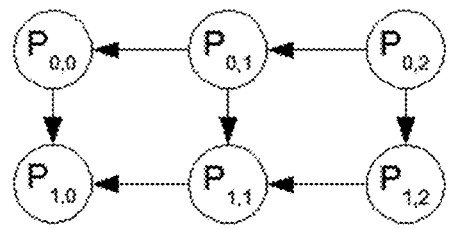
FIG. 3A illustrates ordering matrix of $\Theta_1$.
Figure 3B:
FIG. 3B illustrates ordering matrix of $\Theta_2$.
Figure 3C:
FIG. 3C illustrates ordering matrix of $\Theta_3$.
Figure 3D:
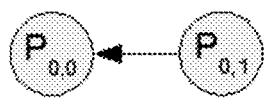
FIG. 3D illustrates ordering matrix of $\Theta_4$.
Figure 3E:
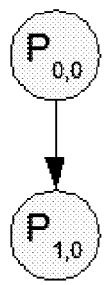
FIG. 3E illustrates ordering matrix of $\Theta_5$.

The generalization performance of a learned Bayesian network largely depends on the quality of the prior provided to the learning machine. Indeed, the prior distribution is designed to provide additive domain expert knowledge to the parameters in a Bayesian network which tolerate some variance around these initial counts. The learning task is combinatorial regulates on this initial counts by the data statistics. The use of a prior distribution becomes even more important in case of scarce data.

One essential problem in specifying Dirichlet prior (commonly used in maximum-a-posterior estimation) is that, it is often impossible for a domain expert to accurately specify the parameters of a Dirichlet distribution since they are unintuitive to a domain expert. Consequently, in practice, the parameters of a Dirichlet prior are either randomly assigned or set equally which results either non-informative prior or statistically inaccurate prior. When data is scarce, this inaccurate prior induce additive bias in selecting the single best model.

On the other hand, there is usually qualitative information available from many resources in a domain, such as domain expert, literature, database etc. Such knowledge usually contains validated information describing certain qualitative relations, e.g. inequality or logic, among entities in the domain. This type of qualitative knowledge has been ignored in Bayesian network learning due to their properties of lacking quantitative information which is desired to a learning machine.

Example embodiments of the invention includes a framework for learning parameters in Bayesian networks by integrating generic qualitative domain knowledge with quantitative data. A qualitative information is first translated into mathematic formulations, e.g. constraints. Then Monte Carlo sampling is recruited to reconstruct the quantitative prior distribution out of the qualitative domain knowledge and a novel score is designed to combine the prior distribution with data statistics. The algorithms (QMAP) are tested both in genetic regulatory network in computational biology and in facial Action Unit recognition network in computer vision. The results show that i) with even very generic qualitative domain knowledge, QMAP outperforms drastically ML and MAP estimation; ii) QMAP achieve surprisingly good estimation even with very scarce data and dramatically reduced the dependence on the amount of training dataset.

Methods

A framework is provided for Bayes net parameter learning with generic prior knowledge. In this study, a knowledge model [9, 10] was used to translate the qualitative domain knowledge into a set of inequality parameter constraints. The parameter priori distribution (i.e. priori pseudo counts) was reconstructed from these constraints. A novel Bayesian parameter score function which integrates this prior distribution with the quantitative data statistics was provided. In this way, the parameter posterior distribution is combinatorially regulated by both quantitative data and prior knowledge.

A. Qualitative Constraints

In general, qualitative domain knowledge can define various constraints over conditional probabilities in a Bayesian network. As described before, most of these constraints can be represented by a linear regression function $f(\theta_{ijk}) \leq c$, $i, j, k$ (c is a scaler), where $\theta_{ijk}$ is the conditional probability of the state of ith node being k, given its jth parent configuration. In particular, four types of constraints can be derived from this function.

Range Constraints defines the upper bound and lower bound of any parameter in a Bayesian network:

$$0 \leq \alpha_i TGF\beta_k \leq \theta_{ijk} \leq \beta_{ijk} \leq 1 \quad (1)$$

Cross-distribution Constraints defines the relative relation between a pair of parameters over different conditions. If two parameters in a constraint share the same node index i and value k, but different parent configuration j, the constraint is called cross-distribution constraint. This constraints can be usually derived from causality in the qualitative knowledge.

$$\theta_{ijk} \leq, \geq \theta_{ij'k} \forall j = j' \quad (2)$$

Intra-distribution Constraints defines the relative relation between a pair of parameters under the same conditions. If two parameters in a constraint share the same node index i and parent configuration j, at different value k, the constraint is called intra-distribution constraint. Parameter sharing constraint [6,7,8] is an example of this type.

$$\theta_{ijk} \leq, \geq \theta_{ijk'} \forall k = k' \quad (3)$$

Inter-distribution Constraints defines the relative relation between a pair of parameters under the same conditions. If two parameters in a constraint do not share any of node index i, parent configuration j and value k, the constraint is called inter-distribution constraint.

$$\theta_{ijk} \leq, \geq \theta_{i'j'k'} \forall i = i', j = j', k = k' \quad (4)$$

B. Qualitative Bayesian Parameter Score (QBPS)

In this section, a posterior probability of parameter incorporating both quantitative data and these prior constraints was provided, and this score function was named as Qualitative Bayesian Parameter Score (QBPS). The log-form parameter posterior probability given Bayes net structure and a set of qualitative constraints can be written as $$\log Pr(\theta|G,D,\Omega) = \log Pr(D|\theta,G) + \log Pr(\theta|G,\Omega) - c \quad (5)$$

where $\theta$ denotes the parameters in a Bayes net and G is the network's structure. $\Omega$ represents a set of constraints in qualitative prior knowledge as described in section III-A. Under same assumptions as [1], i.e. i) iid and complete samples; ii) data follows multinomial distribution; iii) parameter modularity and independency; iv) prior parameter distribution is an exponential family, Eq. 5 can decomposed into data likelihood and parameter prior distribution. The data log-likelihood is adopted from conventional parameter learning method.

$$\log Pr(D|\theta,G) = \sum_{i=1}^{n}\sum_{j=1}^{q_i}\sum_{k=1}^{r_i} N_{ijk} \log \theta_{ijk} \quad (6)$$

where $N_{ijk}$ is the number of occurrence in the training date for the ith node to have a value of k and for its parent to have a value of j.

The parameter prior distribution is described by the qualitative constraint. Based on these constraints, an set of independent priori parameter instances can be sampled and each parameter in the set follows a discrete distribution in the exponential family, such as multinomial distribution. Therefore, the prior parameter distribution can be defined as $$Pr(\theta|\Omega,G) = \alpha \prod_{i=1}^{n}\prod_{j=1}^{q_i}\prod_{k=1}^{r_i} \theta_{ijk}^{M_{ijk}} \quad (7)$$

Given $\Omega$ and G, this set of prior parameters $\theta_{ijk}$ defines a class of independent prior networks, i.e. each parameter in the set uniquely define one prior network. Now, if sample in a prior network A times (A is an arbitrary number), the "success" hits of $(X_i=k, \Pi_i=j)$ exists in the A samples is equal to $M_{ijk} = A \times Pr(X_i=k, \Pi_i=j|G,\Omega)$. Together, the QBPS score can be written as $$Pr(\theta|G,D,\Omega) = \alpha \prod_{i=1}^{n}\prod_{j=1}^{q_i}\prod_{k=1}^{r_i} \theta_{ijk}^{N_{ijk}+M_{ijk}} \quad (8)$$

In this way, each prior network determines a pseudo prior statistic count $M_{ijk}$ and provide soft regulations in conjunction with the data statistics. $M_{ijk}$ is functionally equivalent to the hyperparameters of a dirichlet distribution in the conventional parameter learning methods and a closed form estimation can be easily derived. Consequently, the set of prior networks based on qualitative prior knowledge $\Omega$ augments the statistics in data and define a class of posterior probabilities. A set of posterior probability (QBPS scores) can be obtained by projecting the data statistics onto the prior parameter space defined by inequality constraints from qualitative prior knowledge $\Omega$.

C. Maximization of QBPS Score

In this section, it shows that a class of QBPS scores can be derived given data and qualitative prior knowledge. Each QBPS score is associated with single prior network in the model space defined by the constraints. Thus, the local maximum of each QBPS score can be obtained by computing its derivative and setting the derivative to zero as conventional learning methods. Thus, the local maximum estimation of a QBPS score equals to $$\hat{\theta}_{ijk} = \frac{N_{ijk} + M_{ijk}}{\sum_{k=1}^{K} N_{ijk} + M_{ijk}} \quad (9)$$

where $M_{ijk} = A \times Pr(X_i=k, \Pi_i=j|\Omega)$. Now, it assumes that A and $N_0$ has a ratio $\gamma$, i.e. $A = \gamma \times N_0$, Eq. 9 can be extended as $$\hat{\theta}_{ijk} = \frac{N_{ijk} + \gamma N_0 Pr(X_i=k, \Pi_i=j|\Omega)}{\sum_{k=1}^{K} N_{ijk} + \gamma N_0 Pr(X_i=k, \Pi_i=j|\Omega)} \quad (10)$$

From Eq. 10, it showed that ratio $\gamma$ actually specified the belief-ratio between data statistics and prior knowledge statistics. If $\gamma=0$, it neglects the statistics from the prior knowledge and only trusts the statistics in the data, thus, the estimation in Eq. 10 converges to ML results; If $\gamma=+\infty$, the statistics in the data was neglect and only the prior knowledge was trusted, the results converge to Bayesian inference with only prior knowledge [9,10]. Since the estimation in Eq.8 is a joint effect from both inequality constraints in qualitative prior knowledge and data observation, it was names as a Qualitative Maximum a Posterior (QMAP) estimation.

D. QMAP Estimation

1. QMAP Estimation with Full Bayesian Approach

The posterior probability distribution of Bayesian network models is only defined by its parameter distribution given the network structure (G). As it was shown previously, the qualitative constraints Ω can define a set of constraints in the prior parameter space. By recruiting Monte Carlo sampling, the priori parameter distribution from this set of constraints can be reconstructed and a set of prior networks/models (m) can be obtained which are consistent with the body of the qualitative knowledge. Thus, the final posterior probability of Bayesian network models is defined by this class of prior networks in terms of a set QBPS scores (Eq. 8). To further predict future observations on variable X from the training data (D) and priori constraints Ω, given Bayesian network structure (G), this prediction can be calculated as an integration over the parameter space weighted by its posterior probability.

$$Pr(X|G,D,\Omega) = \int_\theta Pr(X|\theta,G) Pr(\theta|G,\Omega,D) d\theta \quad (11)$$

The posterior probability of the model parameter given data and qualitative prior knowledge, i.e. $Pr(\theta|G, \Omega, D)$, is in turn an integration over all possible prior models (m) in the class defined by Ω, thus, extend Eq. 11 can be extended as $$Pr(X|G,D,\Omega) = \int_\theta Pr(X|\theta,G) \int_m Pr(\theta,m|G,\Omega,D) dm d\theta \quad (12)$$

$$= \int_\theta Pr(X|\theta,G) \int_m \frac{Pr(D|\theta,G) Pr(\theta|G,m) Pr(m|\Omega)}{Pr(D)} dm d\theta$$

$Pr(m|\Omega)$ in Eq 12 is equal to 1 since all the valid prior models (m) are consistent with the prior constraints Ω.

The outer integration can be approximated by its local maximum if it is assumed the QBPS curve for each model is peaky, then the inference can be written as $Pr(X|\hat{\theta}, G)$. With full Bayesian approach, final QMAP estimation of the parameter can be optimized by integrating the set of local QBPS maximums over the prior network space, i.e. selecting the QMAP estimation which maximize the integrated QBPS score.

$$\hat{\theta} = \operatorname{argmax}_\theta \left\{ \int_m \frac{Pr(D|\theta,G) Pr(\theta|G,m) Pr(m|\Omega)}{Pr(D)} dm \right\} \quad (13)$$

$$= \operatorname{argmax}_\theta \left\{ \frac{1}{L} \sum_{i=1}^{L} \alpha \prod_{ijk} \theta_{ijk}^{N_{ijk}+M^l_{ijk}} Pr(m|\Omega) \right\}$$

Note that each prior network m uniquely associate with a pseudo prior statistical count $M_{ijk}$. The integration can be approximated in Eq. 13 with Monte Carlo sampling and simplify the estimate as where $Pr(m|\Omega)$ equals to one if $M^1_{ijk}$ is in the class of prior networks defined by qualitative prior knowledge, otherwise, it equals to zero. By taking the derivative of Eq. 13 with respect to $\theta_{ijk}$, the constrained QMAP estimation was obtained with full Bayesian approach as $$\hat{\theta}_{QMAP,FBA} = \frac{1}{L} \left\{ \sum_{l=1}^{L} \frac{N_{ijk} + M^l_{ijk}}{\sum_k N_{ijk} + M^l_{ijk}} \right\} \quad (14)$$

2. QMAP with Frequentist Maximization Approach

On the other hand, given the qualitative prior knowledge and training data, a set of QMAP maximums is derived from multiple prior parameter samples by performing Eq. 10. In practice, this set of prior networks can be retrieved given qualitative constraint with Monte Carlo sampling. Each prior network is associated with an unique $M^1_{i,j,k}$ The final QMAP estimation can be obtained by frequentist maximum approach to select one single best estimate from the parameter posterior probability space. In this way, the maximum from a set of local maximums can be picked up.

$$\hat{\theta}_{QMAP,FMA} \propto \operatorname{argmax}_{\{\theta,l\}} \left\{ \alpha \prod_{ijk} \theta_{ijk}^{N_{ijk}+M^l_{ijk}} Pr(m|\Omega) \right\} = \quad (15)$$

$$\operatorname{argmax}_{\{l\}} \left\{ \frac{N_{ijk} + M^l_{ijk}}{\sum_k N_{ijk} + M^l_{ijk}} \right\}$$

Figure 6A:
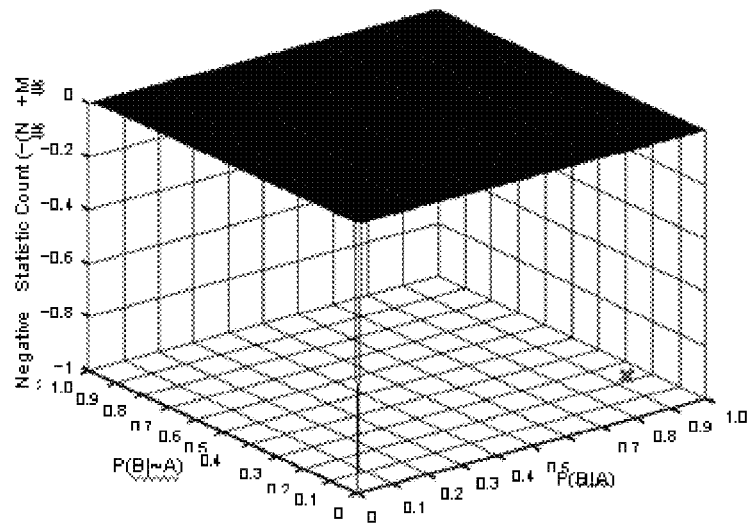
FIG. 6A-6L illustrates parameter learning example in toy network: the network contains two binary nodes. A is an activator patent of B. X,Y-axles represent conditional probability P (B/A) and P (B/A) respectively; Z-axis is equal to the negative value of posterior statistical counts $[-(N_{ijk}+M^1_{ilk})]$ in Eq. 8 with ML, MAP, and QMAP estimation.
Figure 6B:
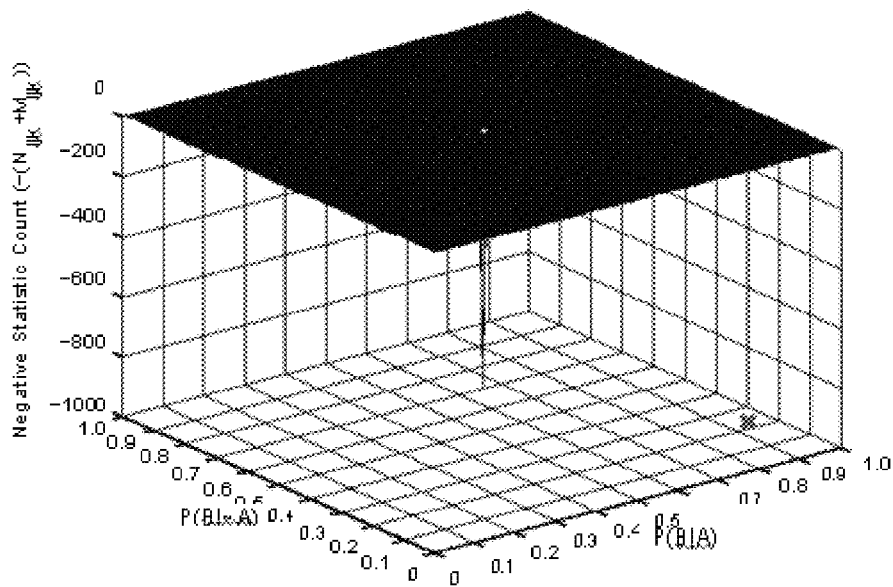
Figure 6C:
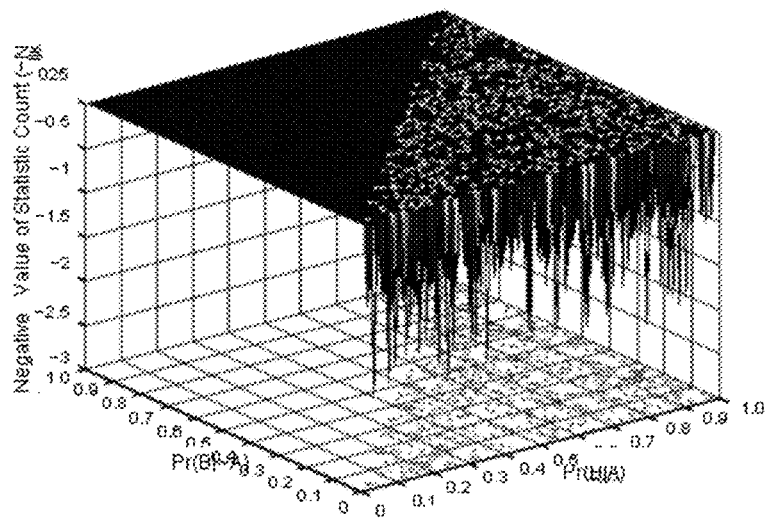
Figure 6D:
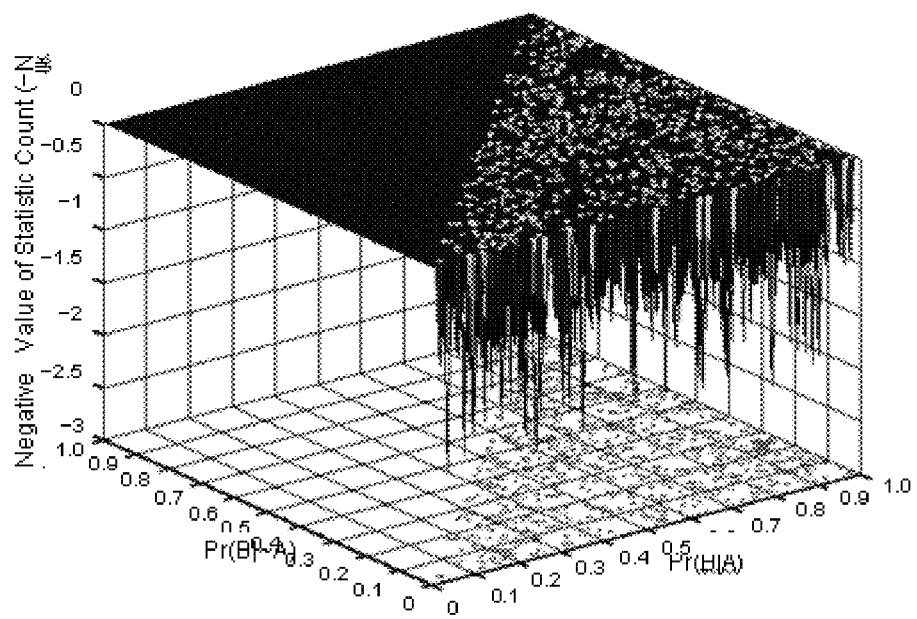
Figure 6E:
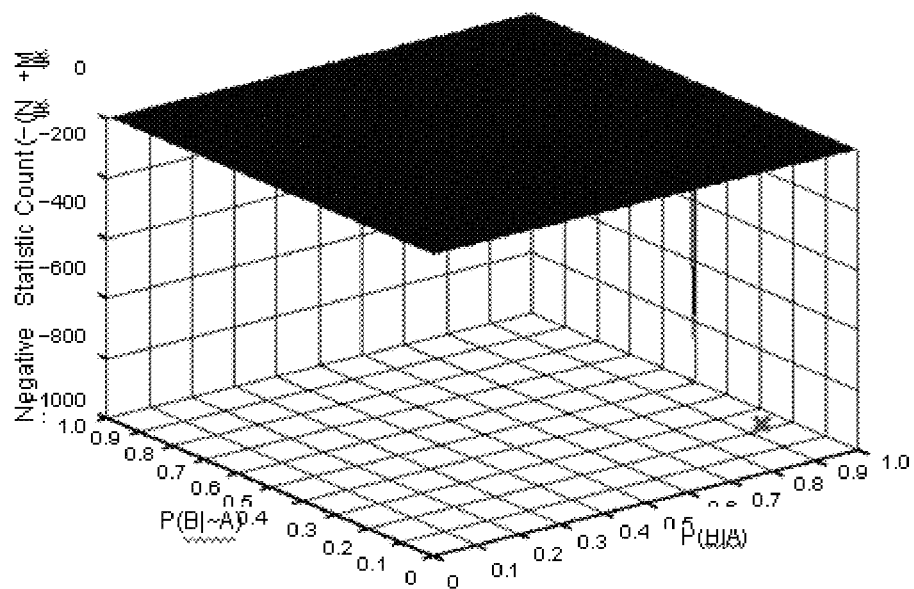
Figure 6F:
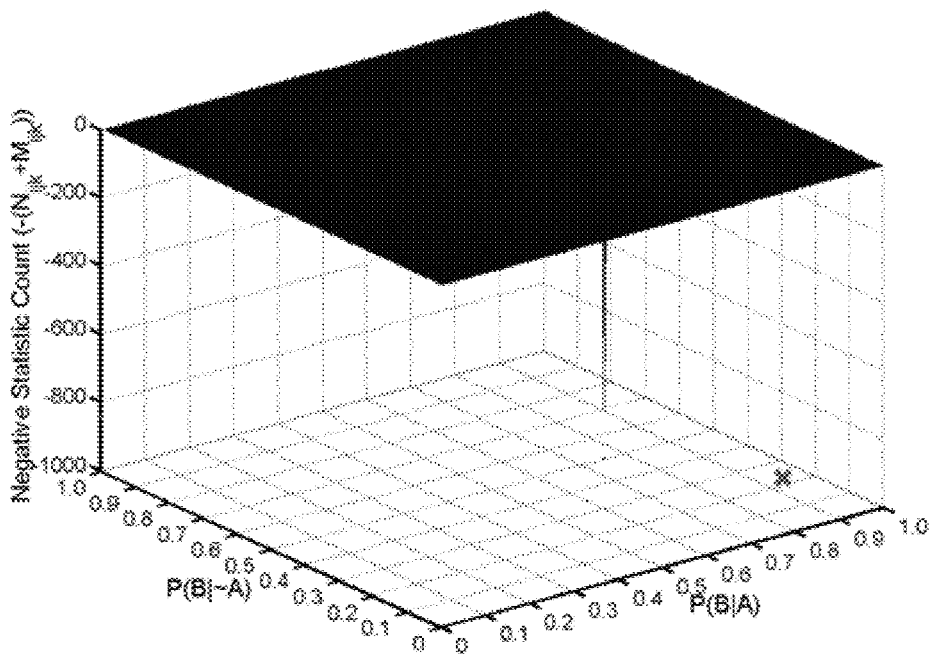
Figure 6G:
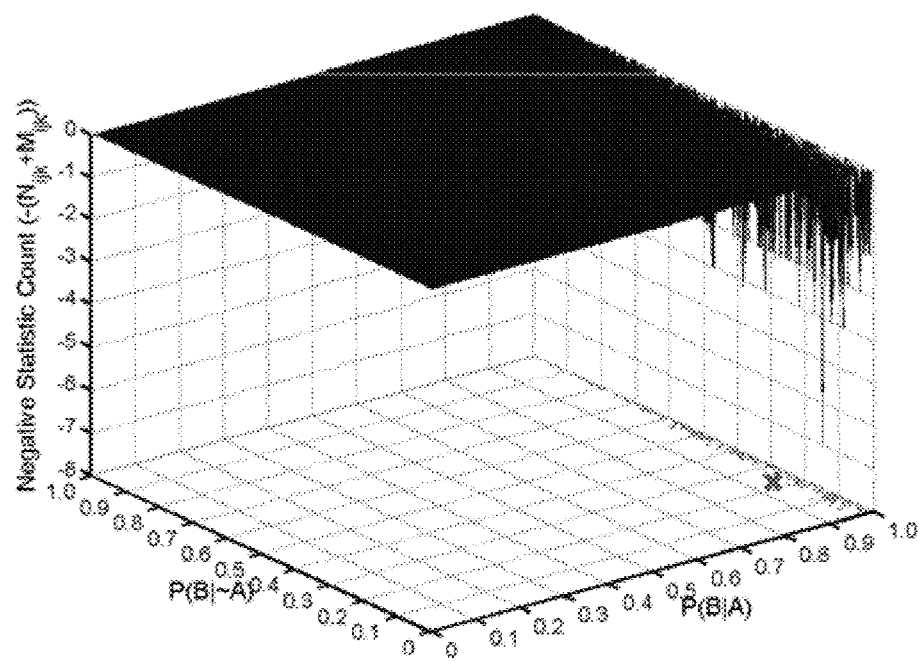
Figure 6H:
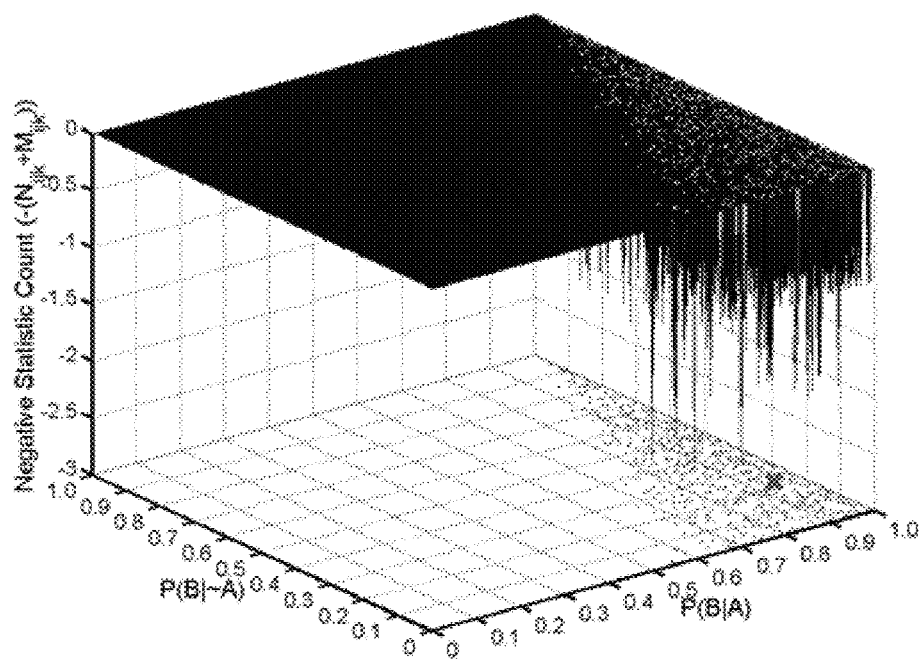
Figure 6I:
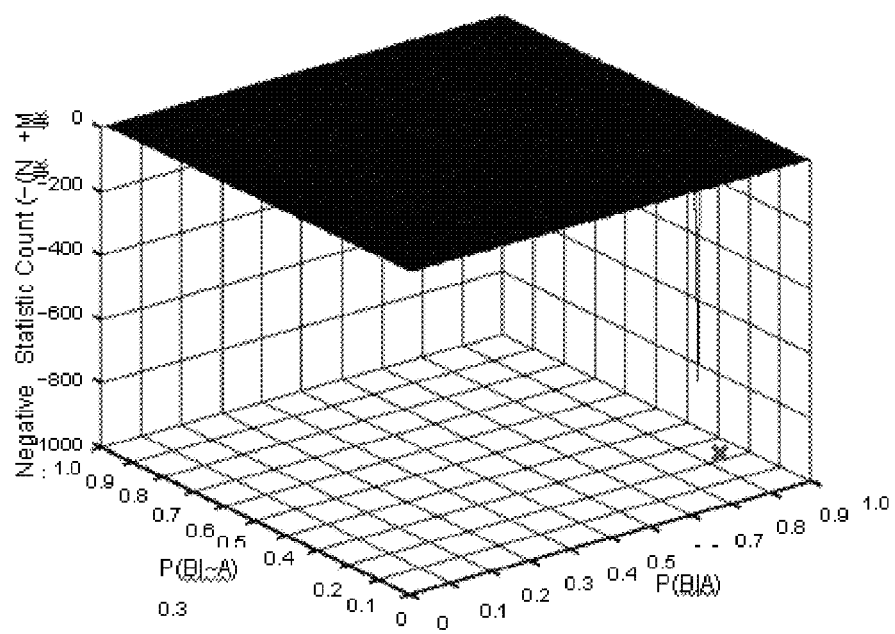
Figure 6J:
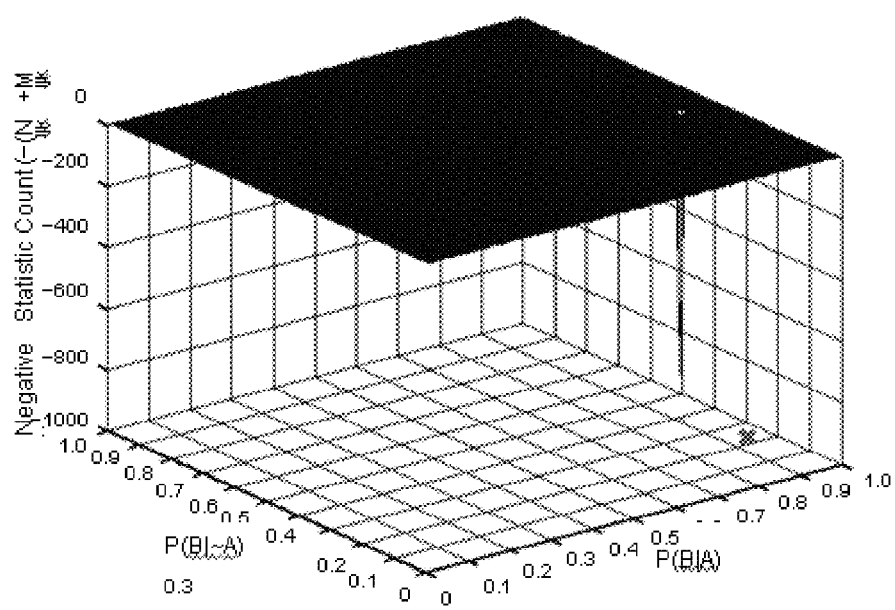
Figure 6K:
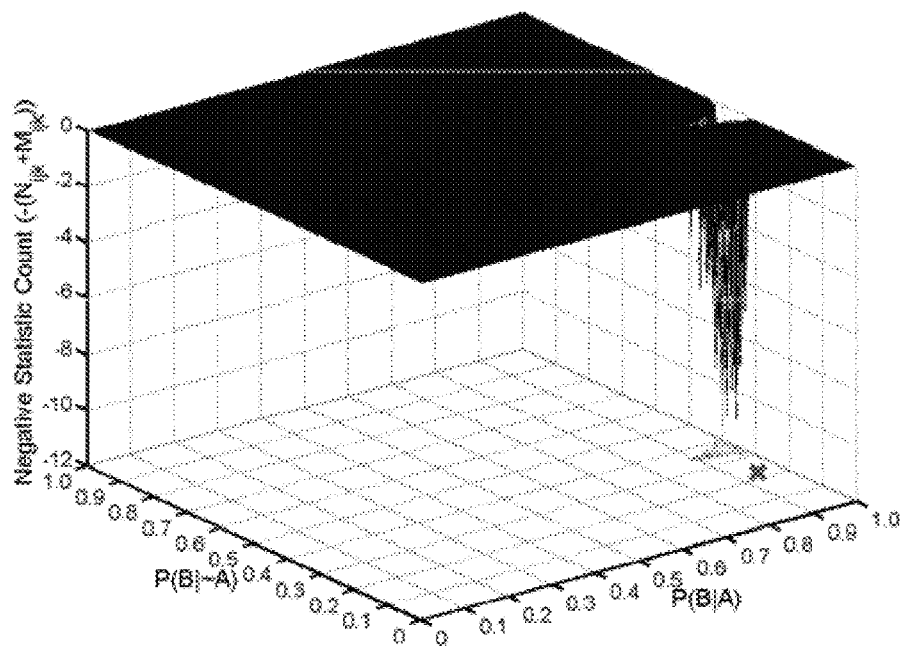
Figure 6L:
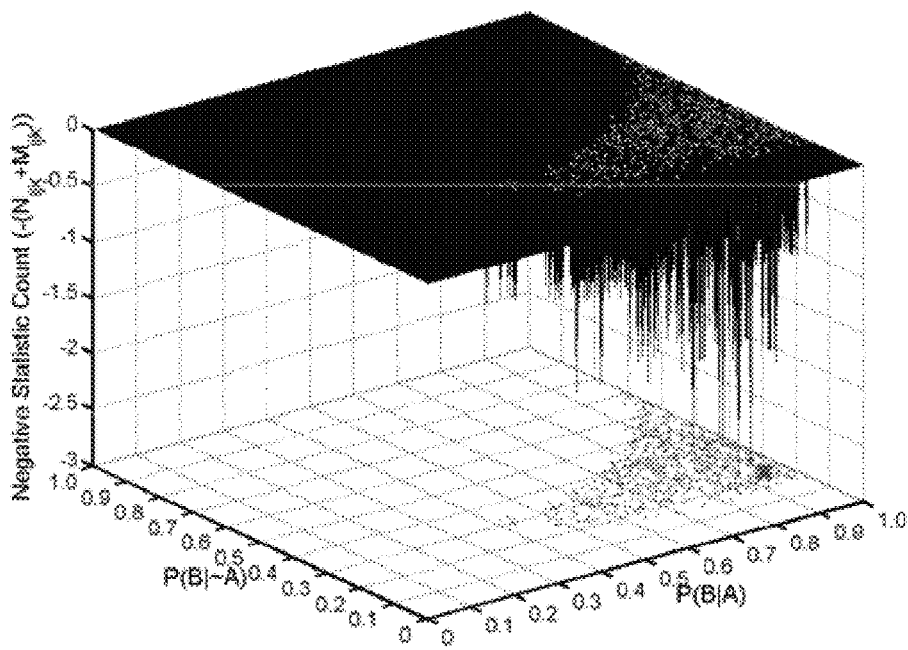

FIG. 6A-6L illustrates parameter learning example in toy network: the network contains two binary nodes. A is an activator patent of B. X,Y-axles represent conditional probability P (B/A) and P (B/A) respectively; Z-axis is equal to the negative value of posterior statistical counts $[-(N_{ijk}+M^1_{ijk})]$ in Eq. 8 with ML, MAP, and QMAP estimation. An example plot of posterior statistical counts in Eq. 8 is shown in FIG. 6. In case of ML learning, the $M^1_{i,j,k}$ is equal to zero for all i,j,k. In case of MAP learning, a typical scenario was simulated, where the dirichlet parameters is set equally to a scalar. In this case, the dirchlet parameters tends to smooth the posterior score by adding equal amount of pseudo counts for all i,j,k. The smoothed posterior favors to the uniformly distribution in this case. By setting these prior pseudo counts to 1, conventional MAP methods try to minimize this biased smooth effects. However, the bias remains significant when the training data is relative small. In FIGS. 6K and 6L, it showed that the QMAP methods augment the posterior distribution by reconstructing the prior from the qualitative knowledge and each prior distribution sample $M^1_{i,j,k}$ is combined with the data statistics to regulates posterior counts on equal opportunities. In this way, the multiple local maximums sit in the posterior space can be explored so that the global maximum is ensured to be selected.

Throughout this application, various publications are referenced. The disclosures of all of these publications and those references cited within those publications in their entireties are hereby incorporated by reference into this application in order to more fully describe the state of the art to which this disclosure pertains. Nothing herein is to be construed as an admission that the inventors are not entitled to antedate such disclosure by virtue of prior invention.

To the extent that any definition or usage provided by any document incorporated herein by reference conflicts with the definition or usage provided herein, the definition or usage provided herein controls.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that may be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope of the claims. On the contrary, it is to be clearly understood that resort may be had to various other aspects, embodiments, modifications, and equivalents thereof which, after reading the description herein, may suggest themselves to one of ordinary skill in the art without departing from the spirit of the present disclosure.

EXAMPLES

Example 1

Yeast Cell Cycle Network

Figure 7A:
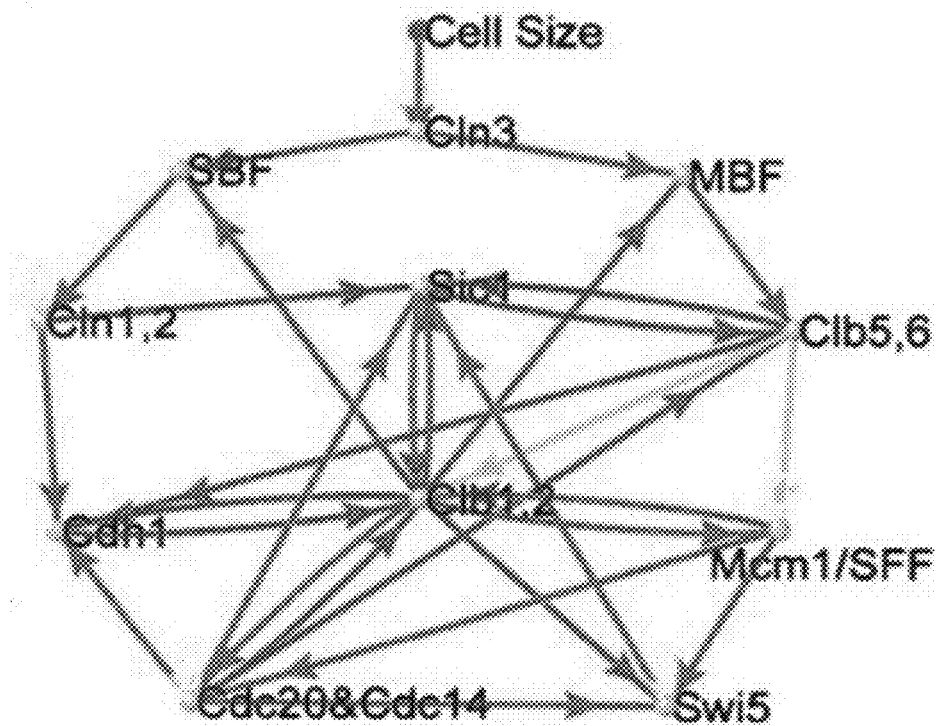
FIG. 7A illustrates parameter learning in yeast cell cycle network.

In this study, the algorithm in a realistic biological network was tested. The transcriptional regulatory network of yeast cell cycle is recently delineated and proven to be robust [17]. In this network in FIG. 7A (the network in [17] was adopted), transcript factors and their target genes form a complex cyclic graph with auto-regulation and feed-back regulation. The dynamic Bayesian network was used to model this biological network. In biological network, the constraints can be formulated based on the natural property of an transcription regulation. As shown in FIG. 7A, color (in greyscales) of every link between two genes indicate either activating or inhibiting regulations. The "green" color denotes activation, i.e. parent gene activates the child gene. While, the "red" color indicates inhibition. If a gene is regulated by multiple parent nodes, $G^P$ denote all the activator parent genes, and $G^N$ denote all the inhibitor parent genes. Then $P(G_i=1|G^P=0,G^N=1) \leq P(G_i=1|G^P=1,G^N=0)$ was obtained. The "yellow" link represent a negative self-feedback regulation which means that this genes' expression level will be inhibited by itself.

Figure 7B:
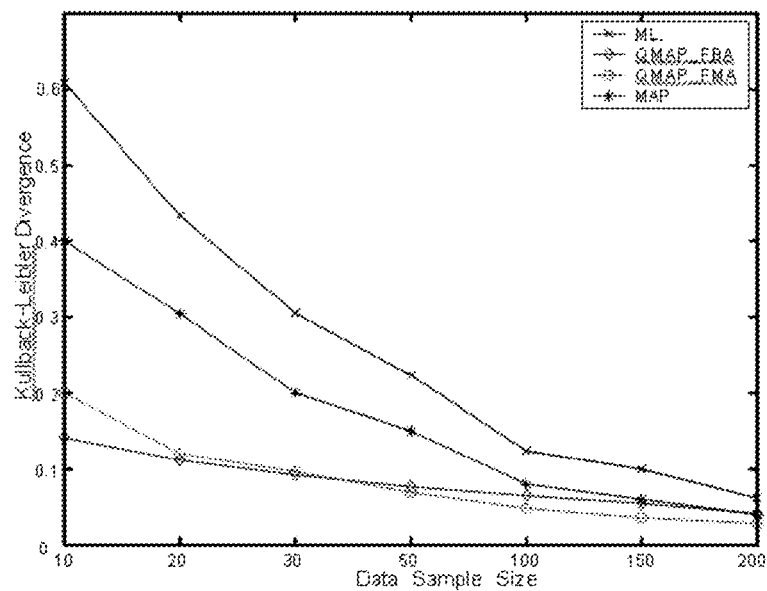
FIG. 7B illustrates KL divergence.

Since the true parameters of this network is not revealed, random probabilities were assigned to the links of this network. For round of each parameter assignment, synthetic temporal datasets were independently generated with representative sample size, i.e. (10, 20, 30, 50, 100, 150, 200). This temporal dataset is used to learn the original parameter assignments. In each learning task, three learning schemes, i.e. ML, MAP (with dirichlet parameter Mijk=1) and QMAP were performed. For each scheme, learning results were calculated by averaging Kullback-Leibler divergence of the learned parameters (under specific sample size) to the actual parameter assignments. This learning process was repeated with various parameter assignments. The final results (mean KL divergence) for each learning scheme with various training samples are shown in FIG. 7B. At 10 training samples, QMAP improves the learning accuracy by more than 3 times to ML estimation and 2 times to MAP estimation. It is shown that QMAP algorithms constantly outperform ML and MAP approach in a dynamic network under all sample sizes. Especially, in case of scarce data (data sample less than 50), the QMAP methods which incorporate the qualitative domain knowledge, significantly improves the estimation accuracy than ML and MAP. To achieve a good learning results, (e.g. KL≤0.1), QMAP requires 30 to 50 samples. To obtain comparable results, ML and MAP requires 100 to 200 samples. Indeed, it can be concluded that, for a parameter learning task in dynamic systems like yeast cell cycle transcription regulatory network, i) QMAP can drastically improve the learning accuracy comparing to ML and MAP. In case of scarce data, QMAP improve the estimation accuracy (in terms of KL divergence) by 2 to 3 times; ii) To achieve a good prediction performance (in terms of KL divergence), QMAP reduce the required temporal data samples by around 3 to 4 times. This is particular valuable for parameter learning tasks in a dynamic system where temporal dataset is hard and expensive to get.

FIG. 8 illustrates a comparison of AU recognition network parameter learning results from ML and QMAP respectively. (a) AU recognition network with AU nodes and measurement nodes; (b) K-L divergence measurement of parameter learning in AU network based on training dataset with various sample size. Comparison of AU recognition skill using the BN leaned from ML and QMAP respective. QMAP to standard ML skills were compared; (c) AU recognition network; and (d) AU recognition skill score at 200 training samples on AU nodes.

Figure 9:
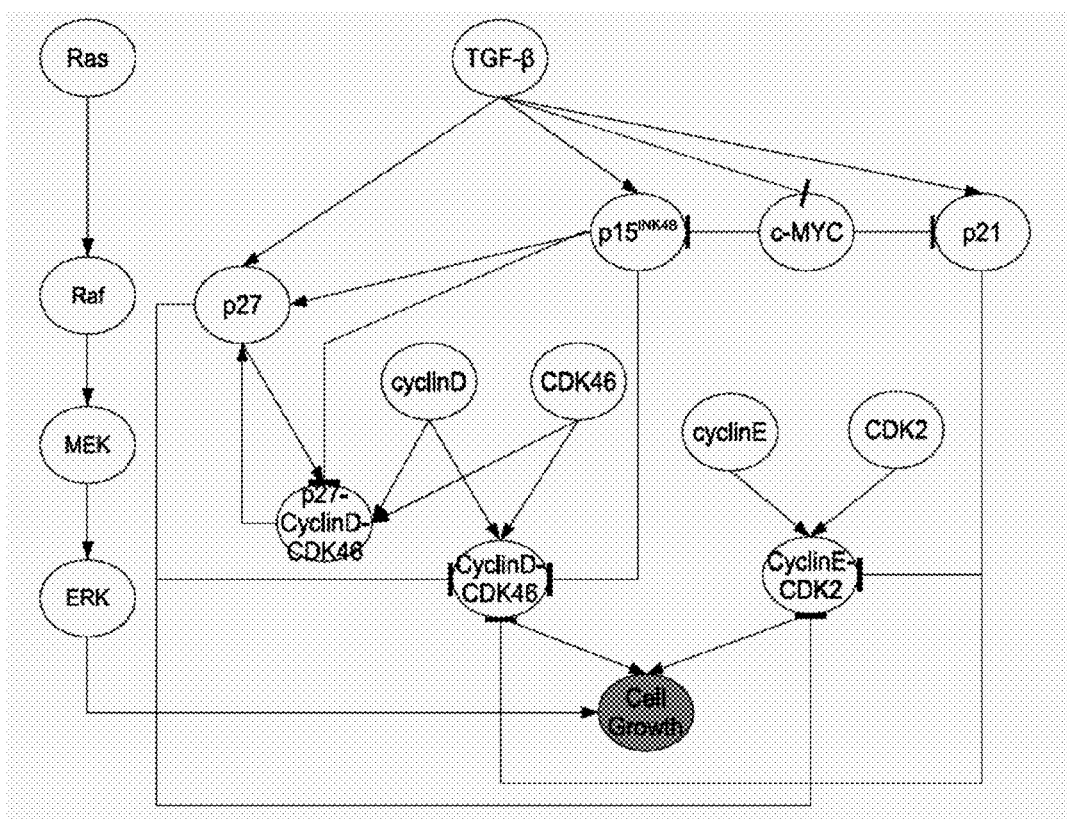
FIG. 9 represents a dynamic Bayesian network.
Figure 10:
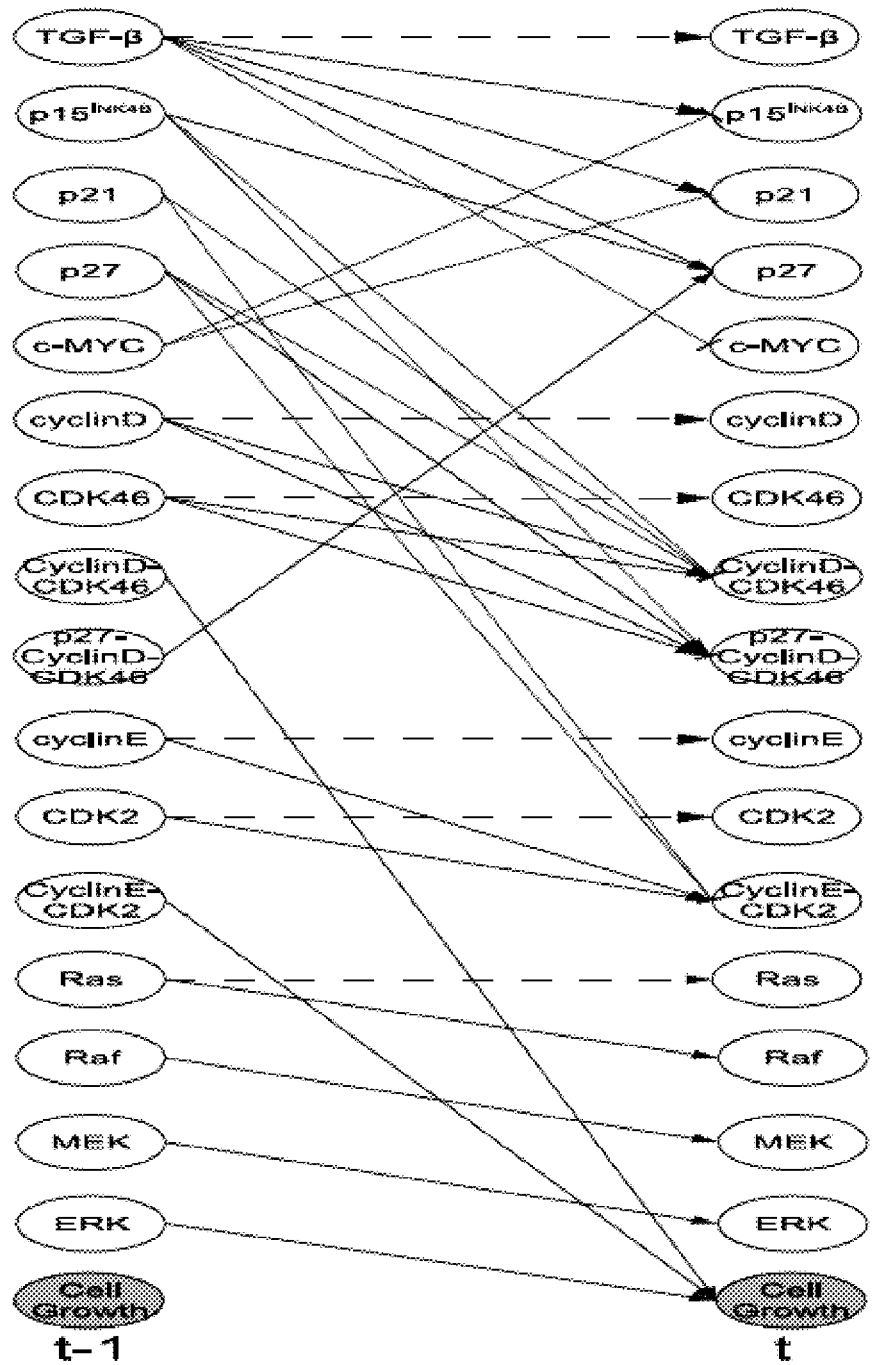
FIG. 10 represents a 2-time-slice Bayesian network in relation to a mammary cell proliferation network.

FIG. 9 represents a dynamic bayesian network, and FIG. 10 represents a 2-time-slice bayesian network in relation to a mammary cell proliferation network. The arrows in FIG. 9 represent activation and flat ends represent inhibition. Cytokine TGFβ inhibits cell growth promoter, c-MYC. In additional, c-MYC promotes cell proliferation by repressing several cell growth suppressor proteins, p15, p21. TGFβ elevates activity of three cyclin-dependent kinase's inhibitor: p15, p21 and p27. p15, p21 and p27 inhibit the complex formation between cyclinD and CDK4,6 and p27, p21 further prevent cyclinE-CDK2's activation. TGFβ elevates expression of CDK4/6-specific inhibitor p15. p27 binds to CDK4,6 to form a complex, meanwhile, p27 is released from this protein complex under the presence of p15. p15 indirectly stimulates the surge of p27. CyclinD1 and CDKs 4,6 form a complex which drives the cell proliferation in combination with complex formed by cyclinE and CDK2. Besides TGFβ pathway, hyperactive Ras signaling regulates cell developments and promotes cell growth.

Figure 11:
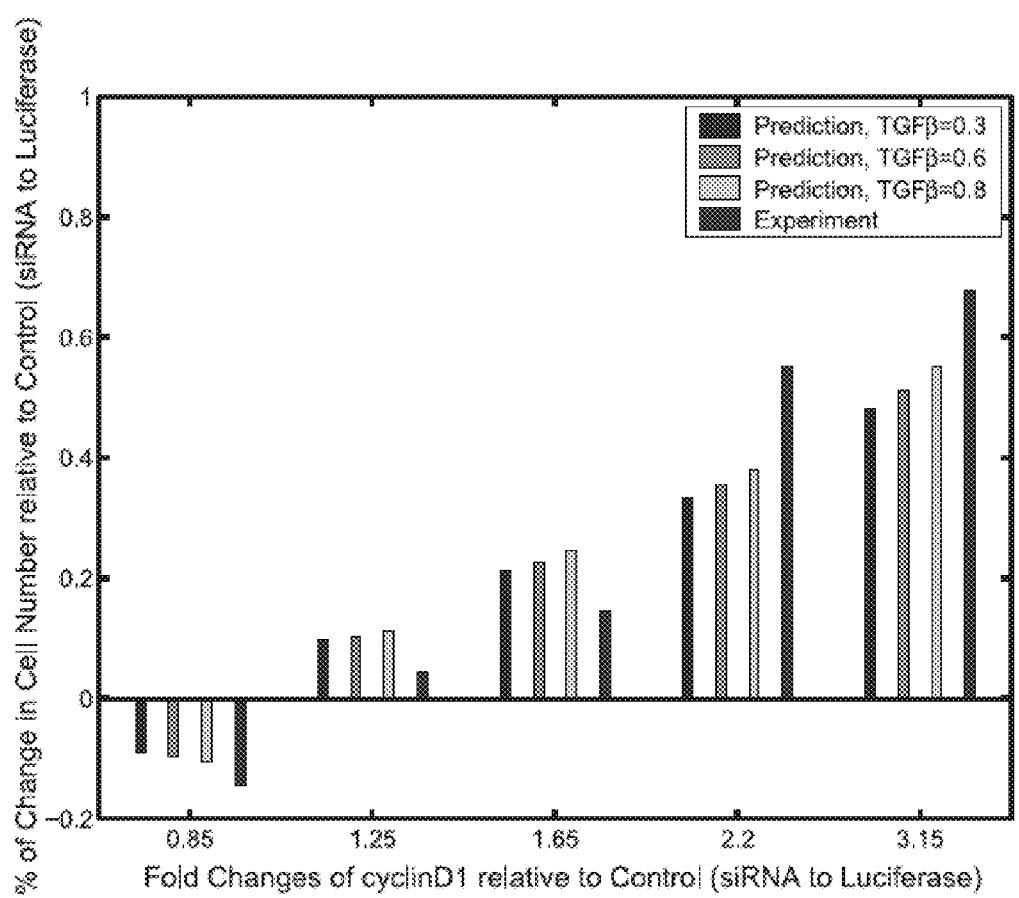
FIG. 11 shows and example prediction on cell proliferation in MCF-7 cell.
Figure 12:
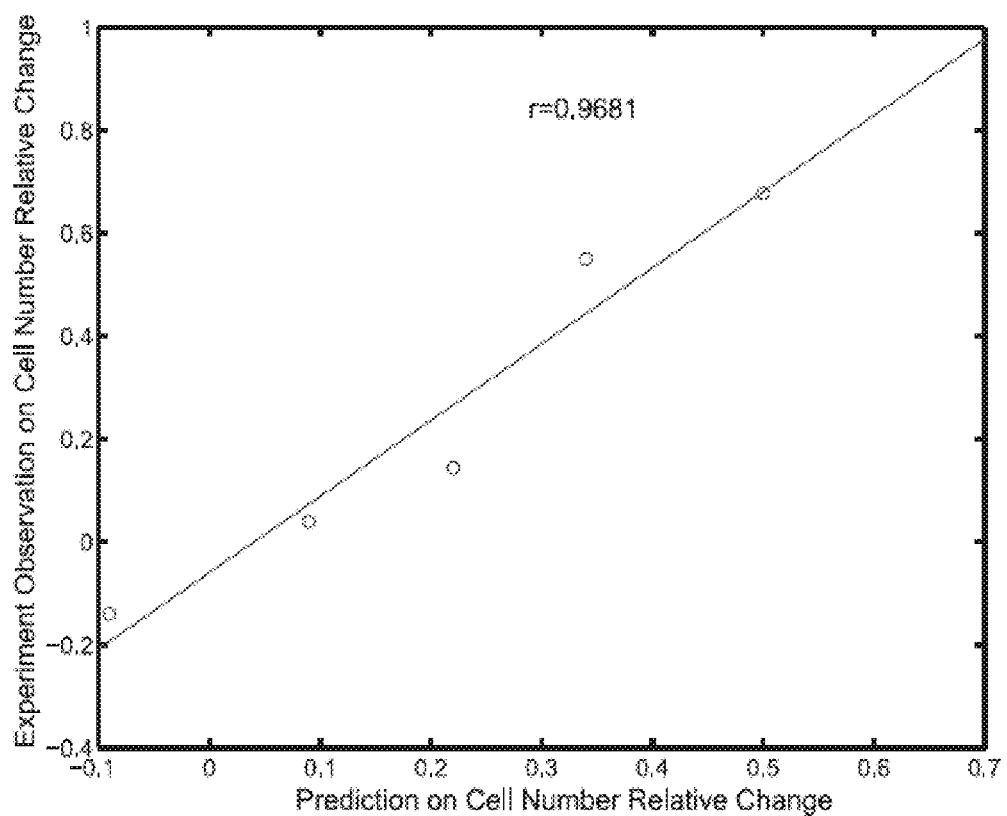
FIG. 12 shows correlation between predictions and experiments.
Figure 13:
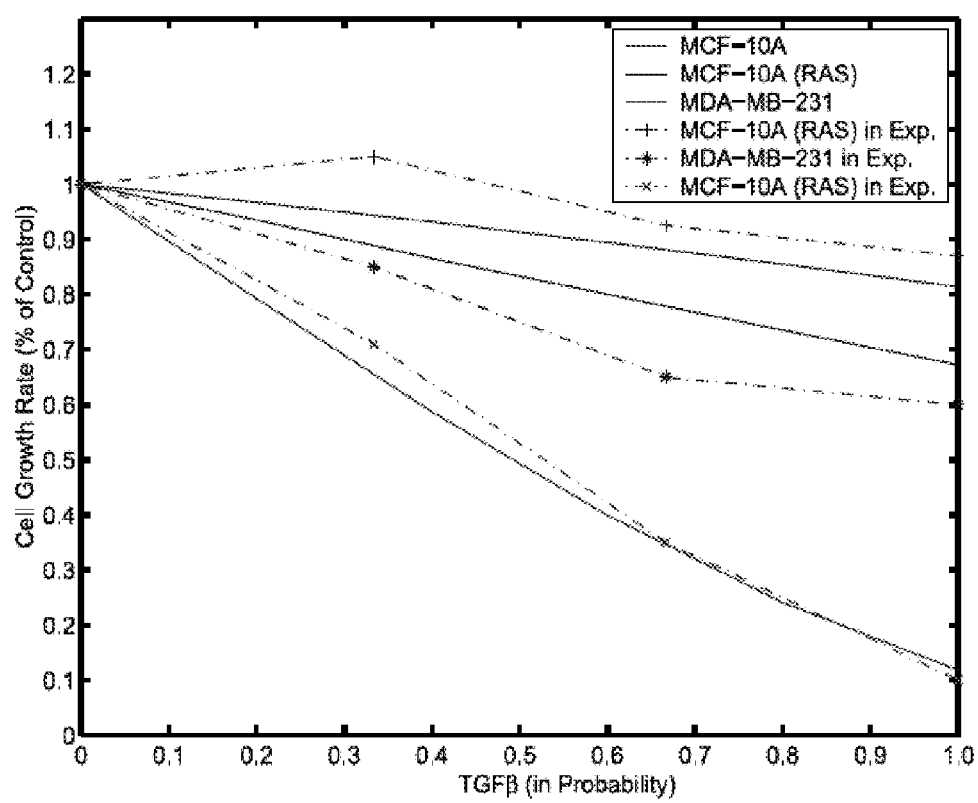
FIG. 13 shows crediction on cell proliferation in three breast normal and cancer cell.
Figure 14:
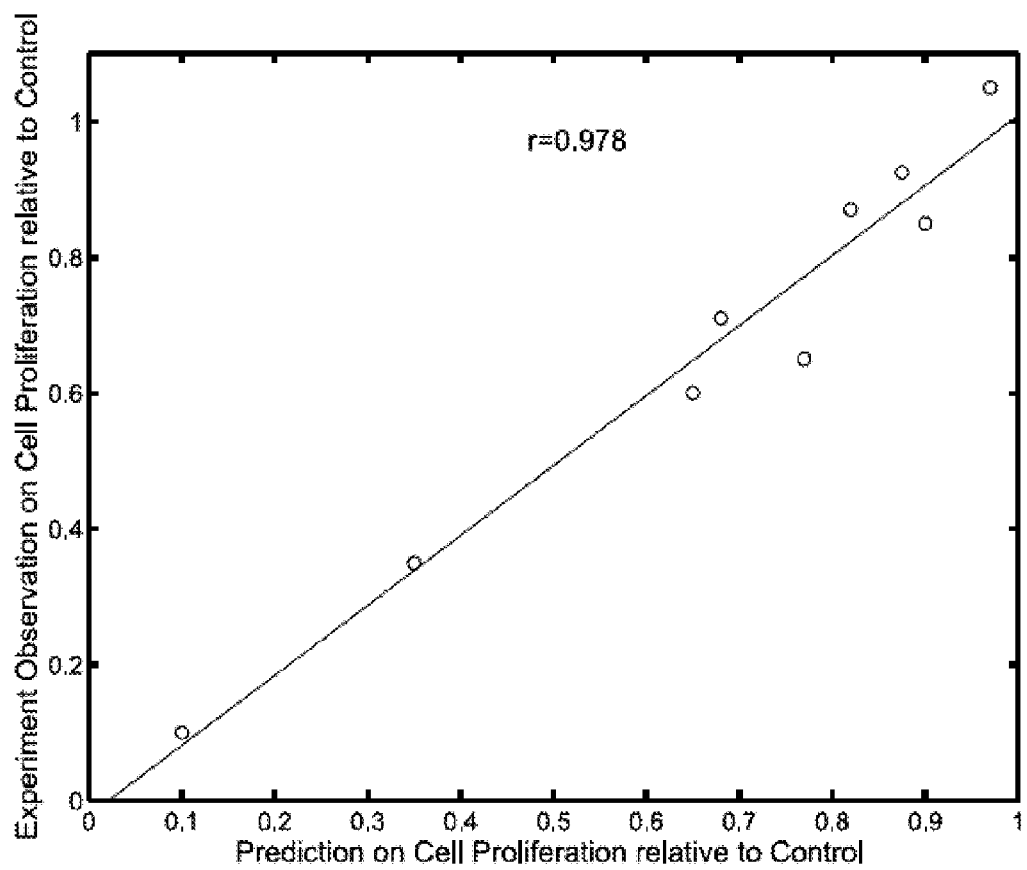
FIG. 14 shows correlation between predictions and experiments.

FIGS. 11-14 represent prediction on cell proliferation efficiency with interfered TGFβ and cyclinD1 in Breast Cancer. FIG. 11 shows and example prediction on cell proliferation in MCF-7 cell. FIG. 12 shows correlation between predictions and experiments. FIG. 13 shows credction on cell proliferation in three breast normal and cancer cell. FIG. 14 shows correlation between predictions and experiments.

Figure 15:
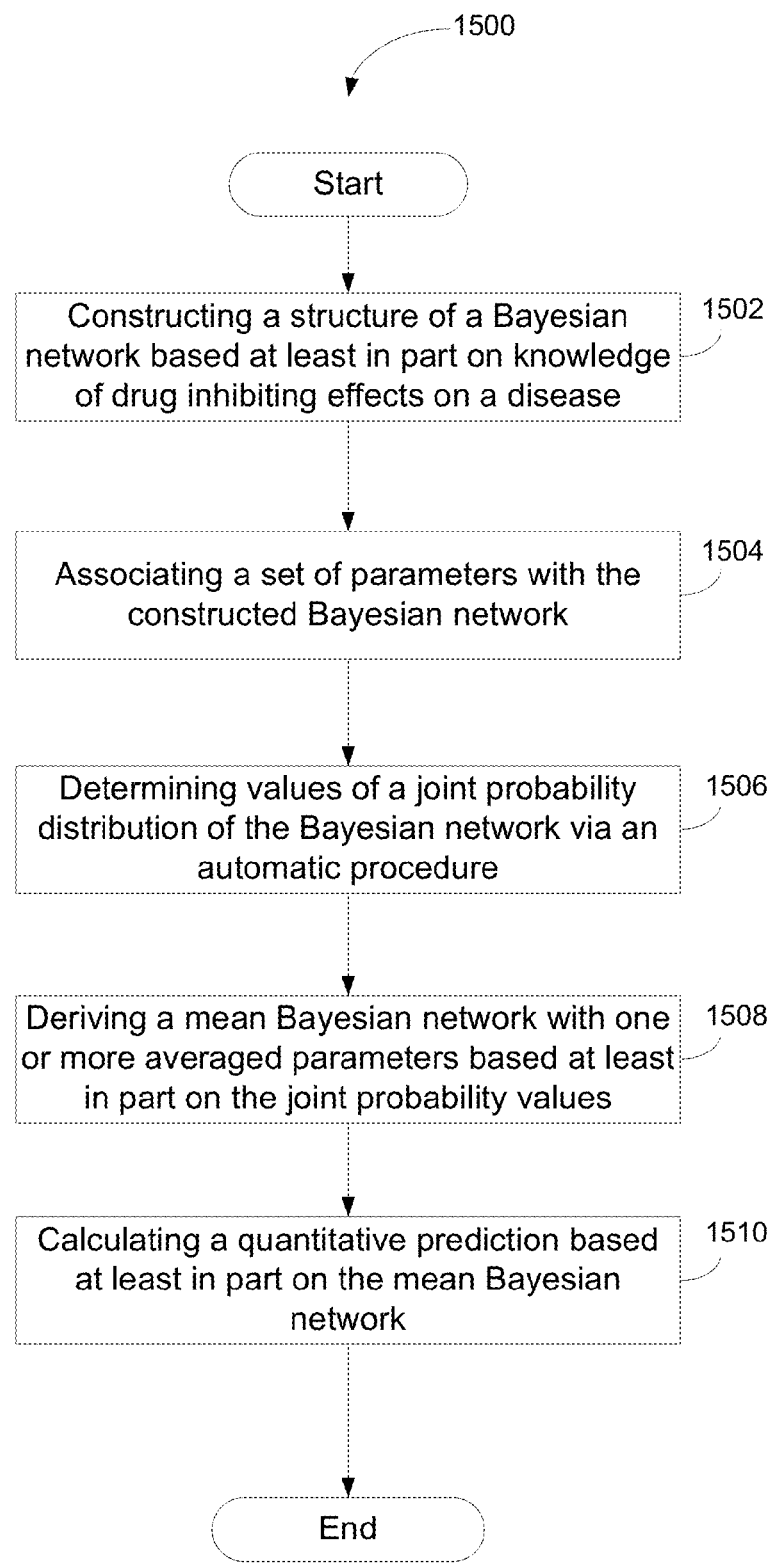
FIG. 15 is a flow diagram of a method, according to an example embodiment of the invention.

An example method 1500 for predicting the effects of drug targets on treating a disease will now be described with reference to the flowchart of FIG. 15. The method starts in block 1502, and according to an example embodiment, includes constructing a structure of a Bayesian network based at least in part on knowledge of drug inhibiting effects on a disease. In block 1504, the method 1500 includes associating a set of parameters with the constructed Bayesian network. In block 1506, the method 1500 includes determining values of a joint probability distribution of the Bayesian network via an automatic procedure. In block 1508, the method 1500 includes deriving a mean Bayesian network with one or more averaged parameters based at least in part on the joint probability values. In block 1510, the method 1500 includes calculating a quantitative prediction based at least in part on the mean Bayesian network. The method 1500 ends after block 1510.

Figure 16:
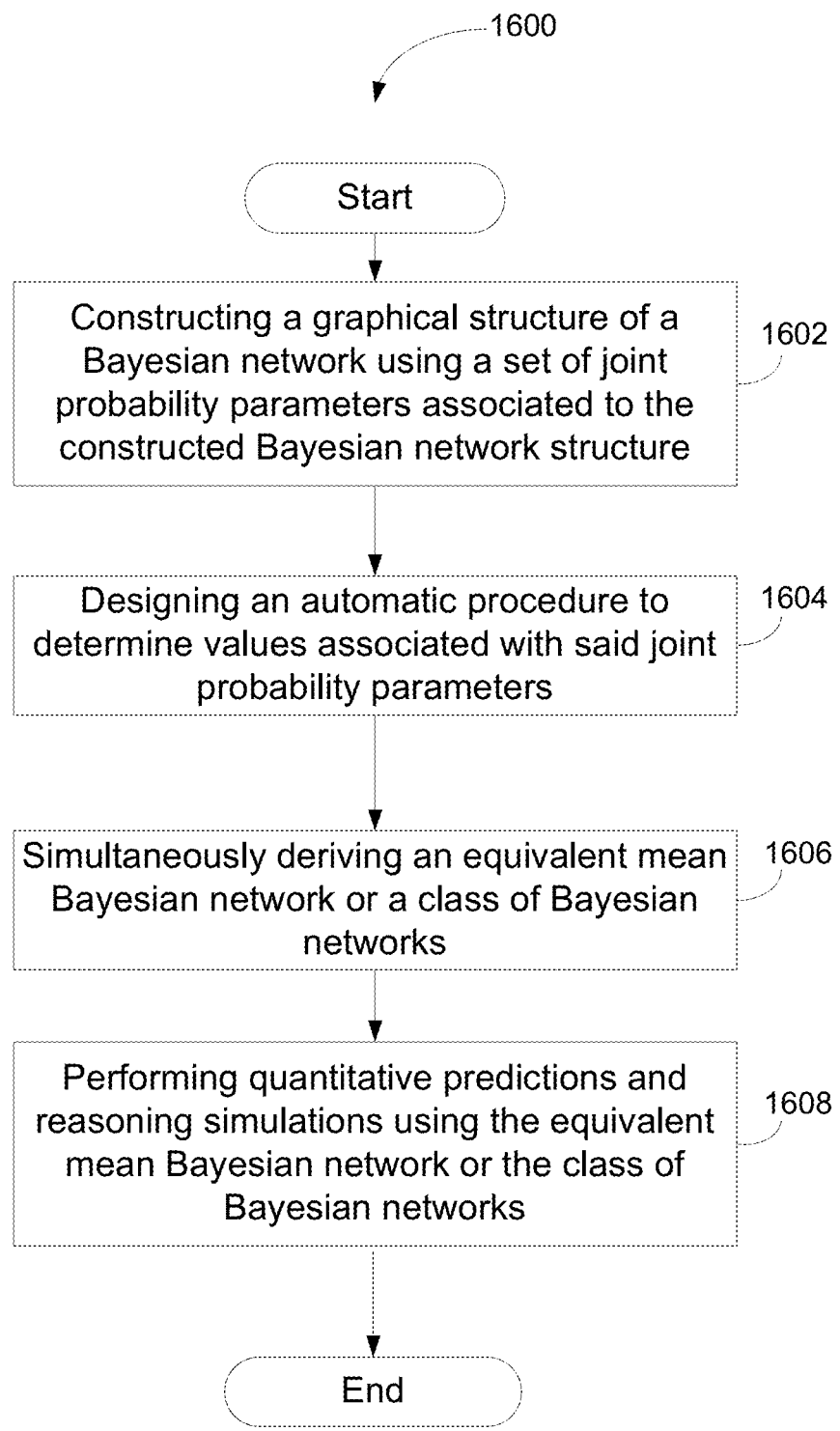
FIG. 16 is a flow diagram of another method, according to an example embodiment of the invention.

Another example method 1600 for automatically determining a multinomial distribution in a Bayesian network will now be described with reference to the flowchart of FIG. 16. The method starts in block 1602, and according to an example embodiment, includes constructing a graphical structure of a Bayesian network using a set of joint probability parameters associated to the constructed Bayesian network structure. In block 1604, the method 1600 includes designing an automatic procedure to determine values associated with said joint probability parameters. In block 1606, the method 1600 includes simultaneously deriving an equivalent mean Bayesian network or a class of Bayesian networks. In block 1608, the method 1600 includes performing quantitative predictions and reasoning simulations using the equivalent mean Bayesian network or the class of Bayesian networks. The method 1600 ends after block 1610.

Example 2

Facial Action Unit Recognition

Figure 8A:
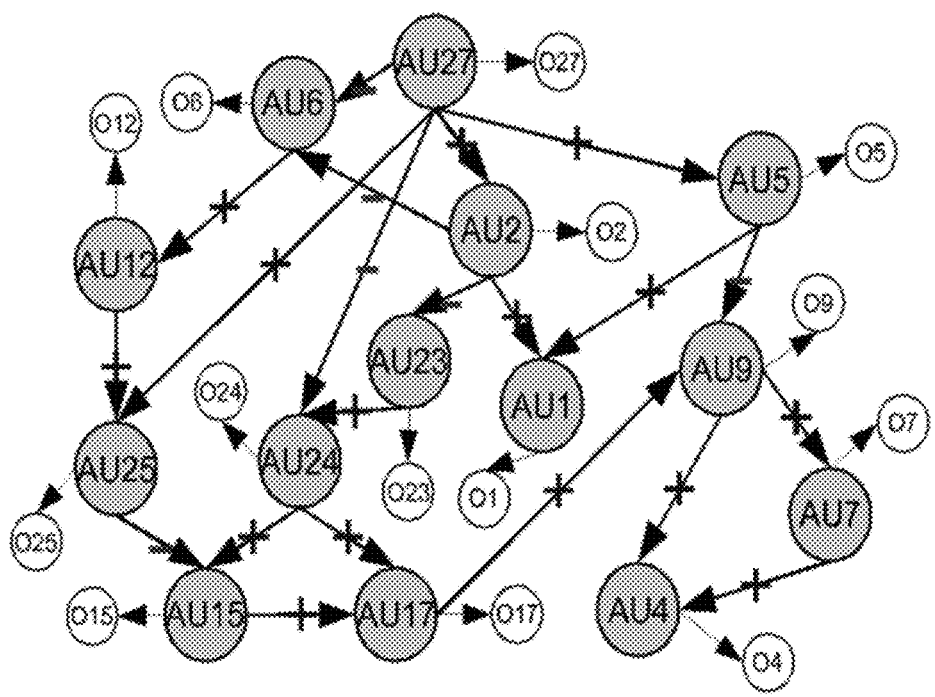
FIG. 8A-8D illustrates comparision of AU recognition network parameter learning results from ML and QMAP respectively.
Figure 8B:
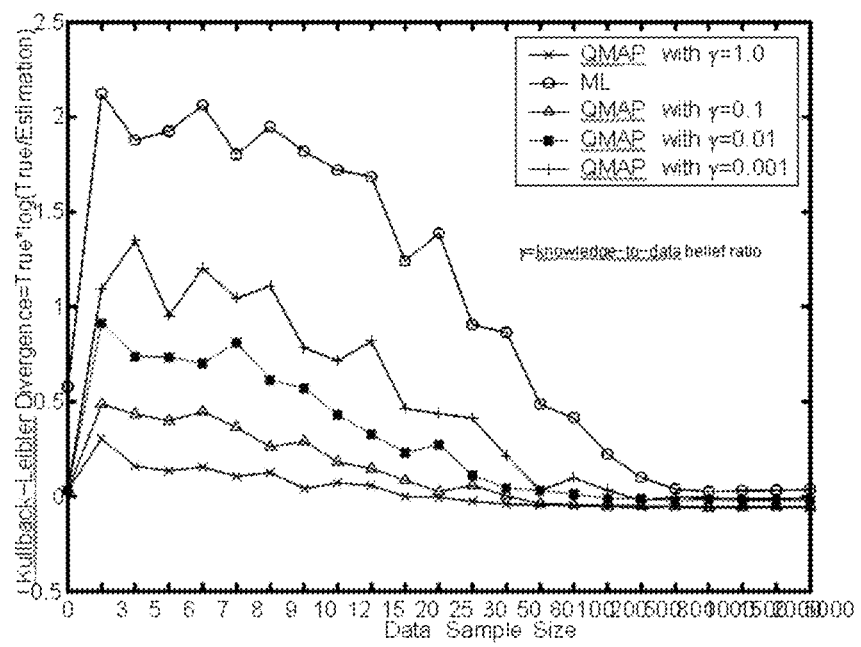

In this study, the invention method was applied to facial action unit (AU) recognition. The Facial Action Coding System (FACS) [14] is the most commonly used system for facial behavior analysis. Based on FACS, facial behaviors can be decomposed into a set of AUs, each of which is related to the contraction of a specific set of facial muscles. Due to the underlying physiology and the facial anatomy, AUs often move in a coordinated and synchronized manner in order to produce a meaningful expression. To represent the dependencies among AUs, Tong et al [16] proposed to use Bayesian network to capture the relationships among AUs. Following the work of Tong et al., the same Bayesian network model was used to capture the relationships among the 14 most common AUs as shown in FIG. 8A, where the larger circular nodes in the model represent AUs while the smaller nodes represent their image measurements. It was demonstrated that the Bayesian network model is superior to the state of the arts AU recognition method. But to use the model, a large amount of training data are needed, which is often hard to acquire. The present invention method shows that the comparable results can be achieved using only a fraction of Tong et al's training data. Similar to the study in biological networks, constraints were extracted based on the following rules provided by domain experts:

1. Marginal Constraint: In spontaneous cases, some AUs rarely occur. One example for this case is AU27, and the rule is $P(AU27=1) \leq P(AU27=0)$, where 1 means presence and 0 means absence.
2. Causality-derived Cross-distribution Constraint: As shown in FIG. 8A, every link between two AU nodes has a sign provided by the domain expert. The + sign denotes positive influence, which means two AU nodes have co-occurrence relationship, while a negative sign denotes negative influence, which means the two AU nodes have mutual exclusive relationship. Considering an AU node AUi has only one parent node AUj, if the sign of the link is positive, $P(AUi=1|AUj=0) \leq P(AUi=1|AUj=1)$ can be generated. If the sign of the link is negative, then $P(AUi=1|AUj=1) \leq P(AUi=1|AUj=0)$ can be generated. If an AU node AUi has more than one AU parent nodes, $AU^P$ denote all the parent nodes with positive links, and $AU^N$ denote all the parent nodes with negative links. Then $P(AUi=1|AU^P=0, AU^N=1) \leq P(AUi=1|AU^P=1, AU^N=0)$ can be obtained.
3. Range Constraint: If an AU node AUi has more than one parent nodes $AU^P$, and all of them with positive influence, then $P(AU_i=1|AU^P=1) \geq 0.8$. If an AU node $AU_i$ has more than one parent nodes $AU^N$, and all of them with negative influence, then $P(AU_i=1|AU^N=1) \leq 0.2$.

Please note the above constraints are due to either facial anatomy or due to certain facial patterns. They are generic enough to be applied to different databases and to different individuals.

A. AU Recognition Network Learning

The 8000 images used in experiments are collected from Cohn and Kanades DFAT-504. In each simulation run, 0 to 5000 samples were randomly selected out of 8000 samples for training and learning task were repeated for 20 times. Training data were used for learning the parameters in the AU Bayesian network (FIG. 8A). After the learning, 1000 untouched samples were selected for testing. Testing data were used to perform AU recognition through inference given learned Bayesian network. The training data is complete.

In the first part, it showed the learning results in K-L divergence on the AU subnetwork in FIG. 8A. In the second part, the real classification results were shown. ML and QMAP estimation were applied with qualitative domain knowledge defined above to learning the parameters in the AU subnetwork. The K-L divergence was shown in FIG. 8B. The x-axis and the y-axis denote training sample size and K-L divergence respectively. The K-L result is actually the mean K-L divergence which is calculated by averaging the parameter learning results over all randomly selected training samples under each specific sample size. It was seen that: i) QMAP with $\gamma=1$ performs significantly better than ML estimation under every training data size. More specifically, the K-L divergence for ML estimation with 3 training sample is decreased from 2.21 to 0.24 for QMAP with $\gamma=1$. Even at 5000 training samples, the K-L divergence for ML estimation is decreased from 0.04 to close to 0 for QMAP estimation; On the other hand, the results can also be evaluated by counting how many training samples are required to achieve specific desired K-L divergence level for ML, MAP and QMAP method respectively. At 3 training sample, K-L divergence for QMAP estimation is 0.24. In order to obtain equivalent or better K-L divergence level, ML estimation needs 200 samples. At 5000 training sample, K-L divergence for ML estimation is 0.04 which can be achieved by QMAP with 10 samples. These results demonstrate that the invention methods with domain-specific yet generic qualitative constraints, and with a small number of manually labeled data (10) provide similar learning accuracy to the ML estimation as compared with a full training dataset (5000).

The learning results of the present QMAP method shed light over the usage of generic qualitative domain knowledge in learning task. Therefore, in this section, an extreme case of parameter learning was explored by ignoring all training data sample but only employing the set of qualitative constraints (same set of constraints defined above) to learn the AU subnetwork parameters. In this case, the data statistics counts in Eq. 10 is zero due to lack of training data. The parameter estimation is only determined by priori pseudo counts given the qualitative knowledge. The K-L divergence in this case is 0.0308 which is lower than K-L divergence of ML learning with full training data (5000 training samples). Meanwhile, this K-L divergence level corresponds to that of QMAP learning with $\gamma=1$ at 25 data samples.

B. Classification

In this section, the performance of the learning methods was studied by using the learned Bayesian network model for AU classification. For AU classification, the BN model needs to be fed with AU measurements computed from Gabor Wavelet jets. Given the AU measurements, the true states of each AU are inferred using the model parameters learnt with the invention method. Specifically, the AU recognition performance was studied under different amount of training data including the extreme case of using no training data at all, and compare the classification results with those in [16].

Figure 8C:
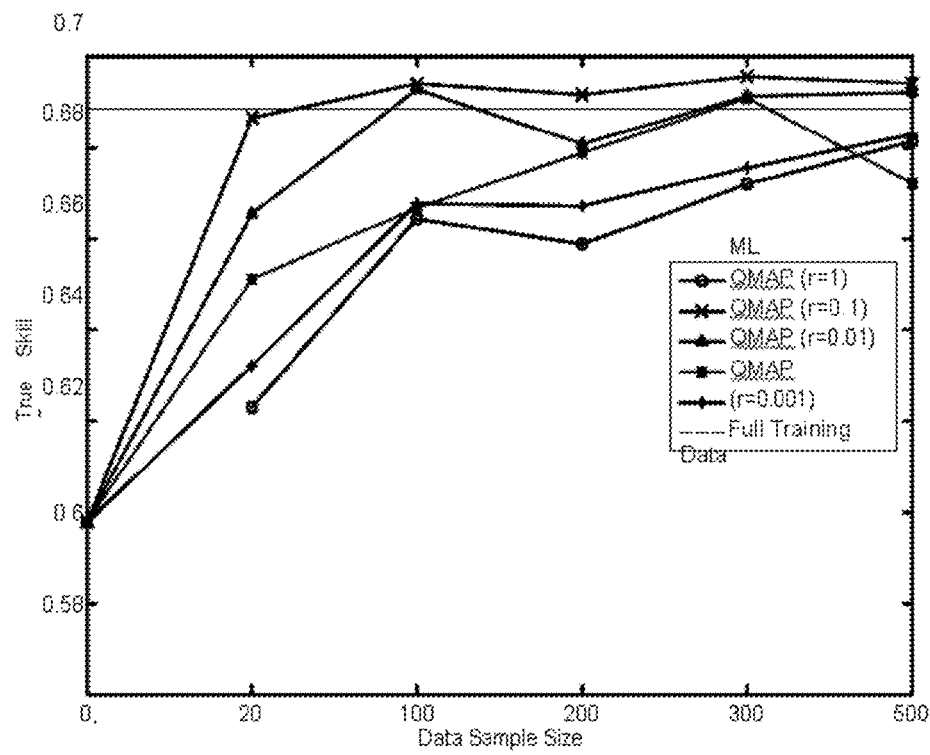

Classification was performed based on the learned AU network from ML and the QMAP approach in above section. For demonstration, the learned AU network parameter was selected under training dataset with representative sample size: 0, 20, 100, 200, 300 and 500. After learning, 1000 untouched data samples were randomly selected for classification test. FIG. 8C shows the AU recognition results. The x-axis represents the training data size for learning AU network parameters (in case of 0 training size, no training data but only qualitative prior knowledge is used for AU network parameter estimation) and y-axis denotes the true skill score (the difference between true positive rate and false positive) respectively. The true skill is calculated by averaging all AU nodes' skill score. It indicates, from FIG. 8C, that the true skill score for QMAP with various belief-ratio ($\gamma$) is significantly better than the skill score for ML estimation under nearly all training data sample size except for QMAP with $\gamma=0.01$. From the above results, it concludes that i) the QMAP estimation by integrating domain-specific yet very generic qualitative prior constraints with quantitative training data significantly improves the AU recognition results comparing to ML estimation at all sample size spanning from sparse data to rich data. This conclusion is particularly true with $\gamma=1$; ii) the QMAP estimations (with different $\gamma$) needs much fewer training samples for AU network to achieve equivalent and even better AU recognition results than ML estimation; iii) Comparing the true skill score of QMAP estimation to the score of ML estimation with full training dataset, it indicates that, with a much smaller number of manually labeled data (around 35 samples), QMAP with $\gamma=1$ can already achieve much better AU recognition results than ML estimation with full training dataset (7000 samples).

In particular, even at sparse training data (20 samples), the average true skill score for all AU nodes increases from 0.6229 for ML estimation to 0.6866 for QMAP with $\gamma=1$, to 0.6655 for QMAP with $\gamma=0.1$, to 0.6512 for QMAP with $\gamma=0.01$ and to 0.6322 for QMAP with $\gamma=0.001$; At 100 training samples, true skill score further enhances from 0.6644 for ML estimation to 0.6940 for QMAP with $\gamma=1$, to 0.6928 for QMAP with $\gamma=0.1$, to 0.6668 for QMAP with $\gamma=0.01$ and 0.6677 for QMAP with $\gamma=0.001$. While training sample size grows to 200, 300, and 500 samples, the true skill score from QMAP with $\gamma=1.0$ is equal to 0.6916, 0.6957 and 0.6942, respectively, and tends to converge. In the same case, ML estimation shows consistently lower classification ability than QMAP. Please note that, using full training dataset (7000 samples for training and 1000 samples for testing), true skill score for ML estimation converge at 0.6883 (shown as the black dashed line in FIG. 8C).

While decreasing the weight on prior knowledge to $\gamma=0.1$, QMAP requires from 80 to 250 training samples to achieve better AU classification results than ML estimation with full training dataset. When $\gamma$ reduces to 0.01, QMAP needs around 300 samples to outperform ML estimation with full training dataset. This number keeps increasing while $\gamma$ reduces. When $\gamma=0.001$, the true skill score of QMAP tends to converge with ML estimation. Therefore, in practice, a larger weight on qualitative prior knowledge is required as long as the knowledge is valid in a domain. The above conclusion is also consistent with the K-L measurements in FIG. 8B.

Figure 4A:
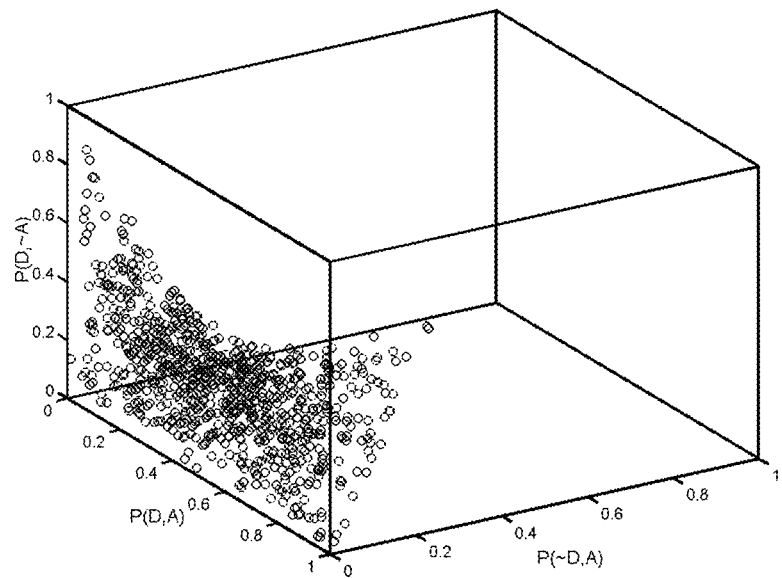
FIG. 4A illustrates joint probability samples.
Figure 4B:
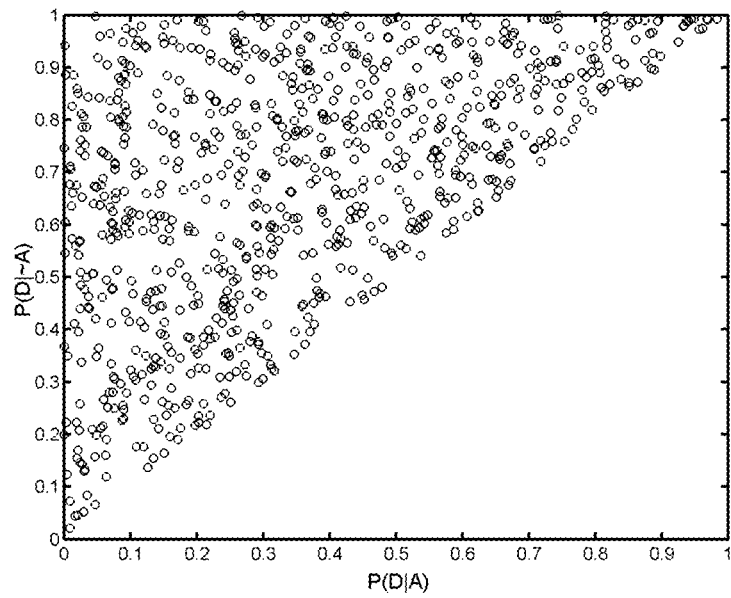
FIG. 4B illustrates conditional probability samples.

FIG. 4a illustrates joint probability samples. In FIG. 4a, the joint probability parameter samples are shown by execution of the second step in the invention procedure. FIG. 4B illustrates conditional probability samples.

Figure 8D:
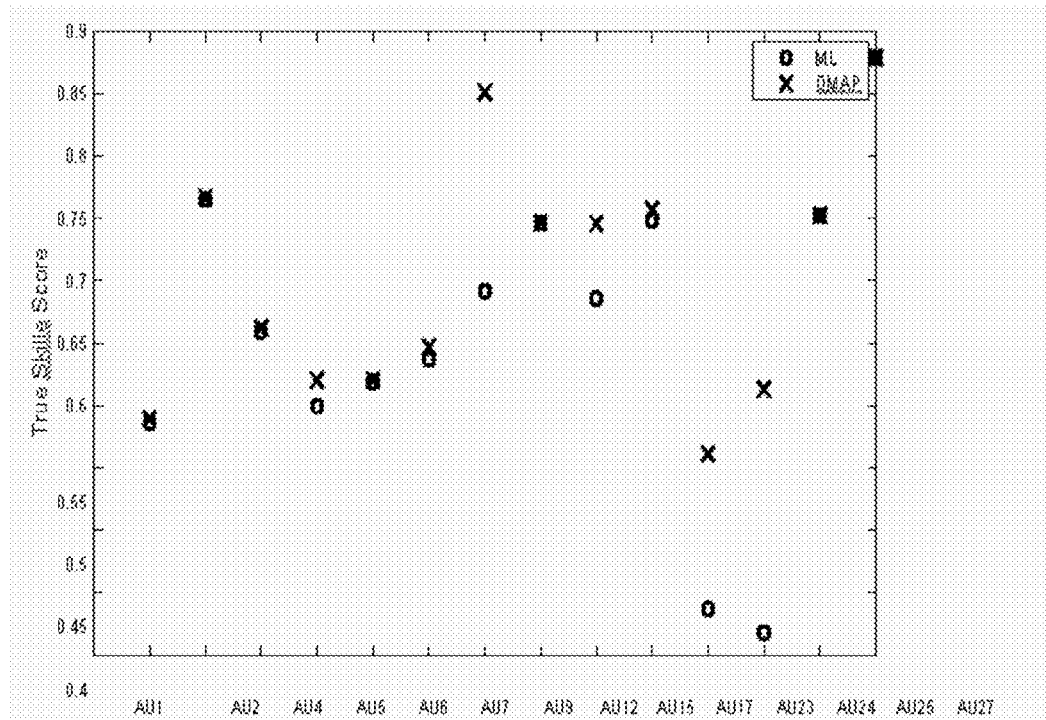

In summary, it is demonstrated that by the invention method, qualitative prior constraints can be integrated into standard Bayesian network parameter learning to achieve significantly improved prediction results. Furthermore, when compared these results with a well developed method in AU recognition [9] by comparing the true skill score of the QMAP method at 200 training samples to the skill score of constrained-ML (CML) estimation (FIG. 4B in [9]) at 300 training samples, while the true skill of each AU node of the QMAP is plot with optimized $\gamma$ is shown in FIG. 8D, it firstly demonstrates that the QMAP approach significantly improves the true skill on AU node number 5, 9, 15, 23 and 24, and slightly improve the skill on AU node 1, 7, 17. The rest skill is equivalent to ML estimation. Comparatively, the invention method boosts the skills on those AU nodes (6, 23, 12, 25, 17, 24, 9, 4) whose skill score is worse than ML estimation in [9].

Therefore, the present invention introduces a novel method for combining qualitative prior knowledge with training data for effective Bayesian network parameters learning. First, different types of constraints can be extracted from domain knowledge. Then, a numerical sampling method was used to capture those constraints as priors on the model parameters. Based on MAP method, a new Bayesian parameter score was developed to combine priors with the training data to estimate the Bayesian parameters. The invention method addressed some of the major shortages of current available methods: i) the cross-distribution inequality constraints, i.e. distribution under different conditions, were incorporated; ii) a soft parameter score in stead of using the hard constraints in a penalty function was developed; iii) by sampling directly on parameter space, the invention algorithm can be more efficient.

The performance of the invention methods in both biology (dynamic network) and computer vision domains (static network) was evaluated. The results show the effectiveness of the invention methods in significantly reducing the dependences on training data while maintaining learning accuracy and in improving the learning accuracy with the same amount of data. Results on the real data for facial action recognition shows that the comparable classification performance using very limited or even no training data was achieved. This is practically important since acquiring training data has proved to be both difficult and expensive. The invention method is important for many other domains where acquiring training data is hard to acquire but qualitative domain knowledge is at hand.

Example 3

Application to Human Embryonic Stem Cells

Figure 5A:
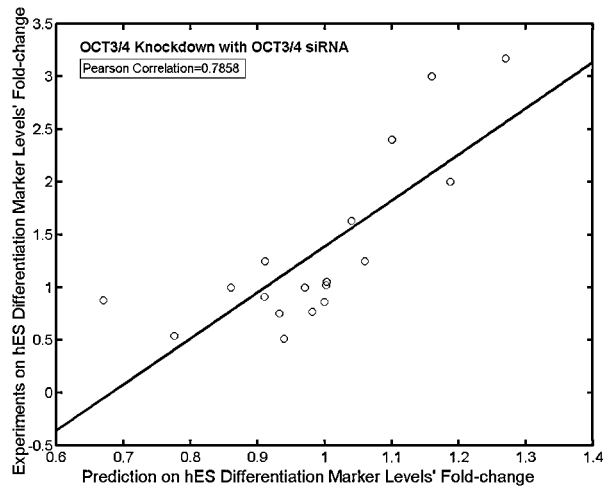
FIG. 5 illustrates correlation between the predicted and experimental gene expression changes of the Oct3/4 marker genes in the human embryonic stem cells.
FIG. 5B illustrates the same for Nanog marker genes.
Figure 5B:
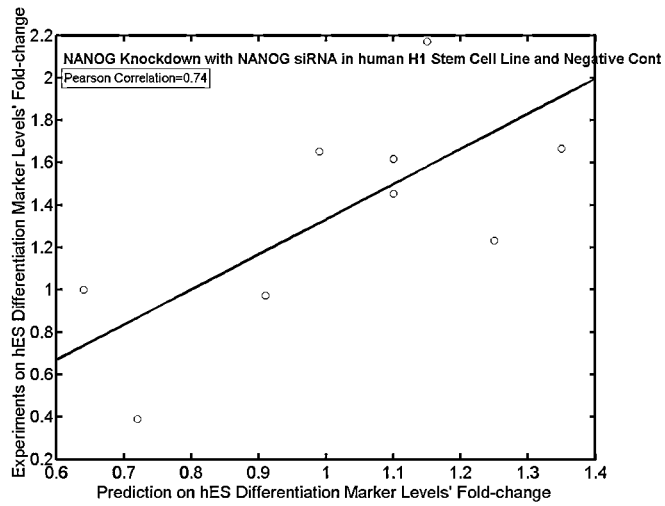

The invention method was applied to human embryonic stem cell (hESC). A demonstration can be found at Stemnet Database (wanglab.ucsd.edu/stemnet). A genetic network, currently only the transcriptional network, that regulates self-renewal and differentiation has been established by collecting knowledge from the literature. The network contains about 100 genes including 23 transcription factors such as the well-known "master" regulators Oct4, Sox2 and Nanog. There are also 8, 6, 4 and 4 marker genes for trophectoderm, endoderm, mesoderm and ectoderm differentiation, respectively. Even thought this network is not complete, computational prediction was conducted on perturbing the network and compared the results with the RNAi experiments (FIGS. 5A and 5B).

Overall, the prediction correlates well with the experimental measurements. Because of the difficulty of developing RNAi against genes in hES cells, there are not many data available for comparison. With the fast advancement of the technology as well as small molecular screening against hESC genes, more experimental data of perturbing the network of self-renewal and differentiation is now readily attainable. The invention method is very useful in designing experiments and searching for reagents to reprogram cell fate.

REFERENCES

[1] D. Heckerman. A tutorial on learning with Bayesian networks. In M. Jordan, editor, *Learning in Graphical Models*. MIT Press, Cambridge, Mass., 1999.
[2] D. Heckerman. Learning Bayesian Networks: The Combination of Knowledge and Statistical Data. *Proc. KDD Workshop*, 1994.
[3] D. Geiger and D. Heckerman. A characterization of the dirichlet distribution through global and local parameter independence. *The Annals of Statistics*, 25:1344-1369, 1997.
[4] R. S. Niculescu. Exploiting parameter domain knowledge for learning in Bayesian networks. *Technical Report CMU-TR-05-147*, Carnegie Mellon University, 2005.
[5] R. S. Niculescu, T. Mitchell, and R. B. Rao. Parameter related domain knowledge for learning in graphical models. *In Proceedings of SIAM Data Mining conference*, 2005.
[6] R. S. Niculescu, T. Mitchell, and R. B. Rao. Bayesian Network Learning with Parameter Constraints. *Journal of Machine Learning Research*, 7:1357-1383, 2006.
[7] R. Chang, M. Stetter, and W. Brauer. Quantitative Bayesian Inference by Qualitative Knowledge Modeling. *The 20th IEEE International Joint Conference on Neural Networks*, IJCNN 2007. [8] R. Chang, W. Brauer, and M. Stetter. Modeling semantics of inconsistent qualitative knowledge for quantitative Bayesian network inference. *Neural Networks*, 21(2-3): 182-192, 2008.
[9] Yan Tong and Qiang Ji, Learning Bayesian Networks with Qualitative Constraints, *IEEE Conference on Computer Vision and Pattern Recognition (CVPR)*, 2008.
[10] F. Wittig and A. Jameson, Exploiting Qualitative Knowledge in the Learning of Conditional Probabilities of Bayesian Networks. *The 16th Conference on Uncertainty in Artificial Intelligence*, USA, 2000.
[11] E. Altendorf, A. C. Restificar and T. G. Dietterich: Learning from Sparse Data by Exploiting Monotonicity Constraints. *The 21st Conference on Uncertainty in Artificial Intelligence*, USA, 2005: 18-26.
[12] Linda van der Gaag, B. Hans and Ad Feelders, Monotonicity in Bayesian Networks. *The 20th Conference on Uncertainty in Artificial Intelligence*, USA, 2004.
[13] Y. Mao and G. Lebanon, Domain Knowledge Uncertainty and Probabilistic Parameter Constraints. *The 25th Conference on Uncertainty in Artificial Intelligence*, USA, 2009.
[14] P. Ekman and W. Friesen. Facial Action Coding System: A Technique for the Measurement of Facial Movement. Consulting Psychologists Press, 1978.
[15] Wenhui Liao and Qiang Ji, Learning Bayesian Network Parameters Under Incomplete Data with Qualitative Domain Knowledge, Pattern Recognition, Volume 42, Issue 11, Pages 3046-3056, 2009.
[16] Yan Tong, Wenhui Liao, Zheng Xue and Qiang Ji, A Unified Probabilistic Framework for Spontaneous Facial Activity Modeling and Understanding, IEEE Conference on Computer Vision and Pattern Recognition (CVPR), 2007.
[17] Fangting Li, Tao Long, Ying Lu, Qi Ouyang and Chao Tang, The yeast cell-cycle network is robustly designed, PNAS, 2004. [18] S. Renooij, S. Parsons, L. C. van der Gaag: Context-specific Sign-propagation in Qualitative Probabilistic Networks. IJCAI 2001: 667-672.
[19] Michael. P. Wellman. Fundamental Concept of Qualitative Probabilistic Networks. *Artificial Intelligence*, 1990.

The invention claimed is:

1. A method, comprising executing computer executable instructions by one or more processors for predicting gene expression profile changes upon inhibiting proteins or genes of drug targets on treating a disease, the method further comprising:
constructing a genetic network comprising a structure of a dynamic Bayesian network based at least in part on knowledge of drug inhibiting effects on a disease;
associating a set of parameters with the constructed dynamic Bayesian network;
determining values of a joint probability distribution of the dynamic Bayesian network via an automatic procedure;
deriving a mean dynamic Bayesian network with one or more averaged parameters based at least in part on the joint probability values; and
calculating a quantitative prediction based at least in part on the mean dynamic Bayesian network,
wherein said method searches for an optimal combination of drug targets whose perturbed gene expression profiles are most similar to healthy cells.

2. The method of claim 1, wherein constructing the structure of the Bayesian network comprises adding directed edges between variables according to domain expert knowledge.

3. The method of claim 1, wherein associating the set of parameters with the constructed Bayesian network comprises denoting joint probabilities of a value of one or more variables in conjunction with values of other variables in the Bayesian network.

4. The method of claim 1, wherein determining values of a joint probability distribution is based on local structures comprising a number of activating parents and a number of inhibiting parents associated with the Bayesian network.

5. The method of claim 1, wherein deriving the mean Bayesian network comprises averaging over joint probability values associated with the network.

6. The method of claim 1, wherein calculating the quantitative prediction comprises integrating over a set of Bayesian networks and multiplying the result by an apriori probability of the Bayesian network set.

7. The method of claim 6, wherein integrating over a set of Bayesian networks comprises applying limits of integration in a relative order based at least in part on a child node probability under a combination of activating and inhibiting parent nodes.

* * * * *